(12) United States Patent
Mao et al.

(10) Patent No.: US 12,421,269 B2
(45) Date of Patent: Sep. 23, 2025

(54) SGLT2/DPP4 INHIBITOR AND APPLICATION THEREOF

(71) Applicant: CGeneTech (Suzhou, China) CO., Ltd., Jiangsu (CN)

(72) Inventors: Qinghua Mao, Shanghai (CN); Tao Yu, Shanghai (CN); Lu Gan, Shanghai (CN); Yi Li, Shanghai (CN); Chengde Wu, Shanghai (CN); Shuhui Chen, Shanghai (CN)

(73) Assignee: CGeneTech (Suzhou, China) CO., Ltd., Jiangsu (CN)

( * ) Notice: Subject to any disclaimer, the term of this patent is extended or adjusted under 35 U.S.C. 154(b) by 913 days.

(21) Appl. No.: 17/629,527

(22) PCT Filed: Jul. 24, 2020

(86) PCT No.: PCT/CN2020/104521
§ 371 (c)(1),
(2) Date: Jan. 24, 2022

(87) PCT Pub. No.: WO2021/018044
PCT Pub. Date: Feb. 4, 2021

(65) Prior Publication Data
US 2022/0242898 A1    Aug. 4, 2022

(30) Foreign Application Priority Data

Jul. 26, 2019  (CN) .......................... 201910683099.2
Feb. 26, 2020  (CN) .......................... 202010119914.5
Jun. 22, 2020  (CN) .......................... 202010572226.4

(51) Int. Cl.
C07H 7/06       (2006.01)
A61P 3/10       (2006.01)

(52) U.S. Cl.
CPC . *C07H 7/06* (2013.01); *A61P 3/10* (2018.01)

(58) Field of Classification Search
CPC ..................................... C07H 7/06; A61P 3/10
See application file for complete search history.

(56) References Cited

U.S. PATENT DOCUMENTS

2010/0022601 A1*  1/2010  Ogawa .................. C07C 323/32
                                                                514/351

FOREIGN PATENT DOCUMENTS

| CN | 101343296 A | 1/2009 |
| CN | 102272136 A | 12/2011 |
| CN | 104854096 A | 8/2015 |
| CN | 105461762 A | 4/2016 |
| EP | 4005568 A1 | 6/2022 |
| JP | 2010504998 A | 2/2010 |
| JP | 2012508746 A | 4/2012 |
| JP | 2012523374 A | 10/2012 |
| JP | 2016504285 A | 2/2016 |
| WO | WO-2010056708 A1 | 5/2010 |
| WO | WO-2011070592 A2 | 6/2011 |
| WO | WO-2012094293 A1 * | 7/2012 | ............... A61P 9/12 |
| WO | WO-2014061031 A1 * | 4/2014 | ............... A61P 3/10 |
| WO | WO-2014081660 A1 | 5/2014 |
| WO | WO-2019134667 A1 | 7/2019 |
| WO | WO-2021018046 A1 | 2/2021 |

OTHER PUBLICATIONS

Sep. 6, 2022 1st OA issued in Mexico counterpart application MX/a/2022/001044.
International Search Report dated Oct. 26, 2020 Issued in PCT application PCT/CN2020/104521.
Written Opinion of International Searching Authority dated Oct. 26, 2020 Issued in PCT application PCT/CN2020/104521.
Aug. 16, 2022 1st OA issued in Japanese counterpart application.
Jul. 6, 2022 1st OA issued in Korean counterpart application.
Nov. 17, 2022 1st OA issued in Australian counterpart application No. 2020320890.
Feb. 16, 2023 Second office Action issued in Mexican Patent Application No. MX/a/2022/001044.
Aug. 4, 2023 EESR issued in European Patent Application No. 20848355.2.

* cited by examiner

*Primary Examiner* — Scarlett Y Goon
*Assistant Examiner* — David H Cho
(74) *Attorney, Agent, or Firm* — Harness, Dickey & Pierce, P.L.C.

(57) ABSTRACT

Compounds as SGLT2/DPP4 dual inhibitors, and application in preparation of medicines as the SGLT2/DPP4 dual inhibitors. A compound represented by formula (I), and an isomer or pharmaceutically acceptable salt thereof are specifically involved.

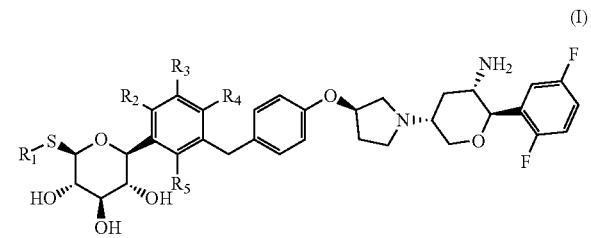

9 Claims, 3 Drawing Sheets

SGLT2/DPP4 INHIBITOR AND APPLICATION THEREOF

CROSS-REFERENCE TO RELATED APPLICATIONS

This application is a U.S. National Phase Application under 35 U.S.C. 371 of International Application No. PCT/CN2020/104521, filed on Jul. 24, 2020, which claims the benefit of Chinese Patent Application No. 201910683099.2, filed on Jul. 26, 2019, Chinese Patent Application No. 202010119914.5, filed on Feb. 26, 2020, and Chinese Patent Application No. 202010572226.4, filed on Jun. 22, 2020. The entire disclosures of the above applications are incorporated herein by reference.

TECHNICAL FIELD

The present disclosure relates to a class of compounds as SGLT2/DPP4 dual inhibitors, and an application in the preparation of a medicament as the SGLT2/DPP4 dual inhibitors. Specifically, the present disclosure relates to a compound of formula (I), an isomer thereof or a pharmaceutically acceptable salt thereof.

BACKGROUND

Diabetes is a metabolic disease characterized by hyperglycemia. Hyperglycemia, in turn, is caused by defective insulin secretion or impairment of its biological action, or both. In diabetes, long-term abnormal blood glucose levels can lead to serious complications including cardiovascular disease, chronic renal failure, retinal damage, nerve damage, microvascular damage, and obesity and the like. In the early stages of diabetes treatment, dietary control and exercise therapy are the preferred control options of blood glucose. When these methods are difficult to achieve the control of blood glucose, insulin or oral hypoglycemic drugs are required for treatment. At present, a variety of hypoglycemic drugs have been used in clinical treatment, mainly including biguanides, sulfonylureas, insulin tolerance improvers, glinides, α-glucosidase inhibitors, dipeptidyl peptidase-IV inhibitors and sodium-glucose cotransport (SGLT2) inhibitors and the like. These drugs have good therapeutic effects, but there are still safety issues in long-term treatment, for example, biguanides are prone to lactic acidosis; sulfonylureas cause hypoglycemic symptoms; insulin tolerance improvers cause edema, heart failure and weight gain; α-glucosidase inhibitors cause abdominal pain, bloating, diarrhea and other symptoms; sodium-glucose cotransporter (SGLT2) inhibitors increase the risk of urinary and reproductive system infections and the like. Therefore, there is an urgent need to develop a new type of safer and more effective hypoglycemic drug to meet the therapeutic needs of diabetes.

Sodium-glucose cotransporters (SGLTs) are a family of glucose transporter proteins found in small intestinal mucosa and renal proximal tubules, and the family members mainly include two main classes of SGLT-1 and SGLT2 proteins. Wherein, SGLT-2 is expressed at high levels in the kidney and is responsible for 90% of renal glucose reabsorption. Inhibition of SGLT2 prevents renal glucose reabsorption, promotes the excretion of glucose through urine, and lowers blood glucose. Since the above processes do not intervene in glucose metabolism, occurrence of hypoglycemic adverse reactions is avoided or mitigated. From 2012 to the present, six drugs, Dapagliflozin, Canagliflozin, Luseogliflozin, Ipragliflozin, Tofogliflozin and Empagliflozin, have been approved for marketing as effective drugs for the treatment of diabetes, moreover, Dapagliflozin, Canagliflozin, and Empagliflozin have been shown to possess cardiovascular benefit or renal protection in the clinic, thereby SGLT2 has become one of the ideal potential targets for the treatment of diabetes. However, SGLT2 drugs also pose an increased risk of urinary and genital infections.

Dipeptidyl peptidase 4 (DPP4) is a serine protease on the cell surface, which inactivates a variety of glucagon-like peptide-1 (GLP-1) and glucose-dependent insulinotropic polypeptide (GIP). DPP4 inhibitors can inactivate DPP4 so that the GLP-1 protein is not decomposed, and it plays a role in controlling blood glucose by increasing the level of GLP-1. So far, several DPP4 inhibitors have been marketed worldwide: sitagliptin, vildagliptin, saxagliptin, alogliptin, linagliptin, gemigliptin and teneligliptin and the like. The marketed DPP4 medicines have weak hypoglycemic effect, and although there is no cardiovascular benefit, long-term data show that they are safe and reliable without significant side effects.

In summary, SGLT2/DPP4 dual inhibitors possess good development prospects.

Content of the Present Invention

The present disclosure provides a compound of formula (I), an isomer thereof, or a pharmaceutically acceptable salt thereof,

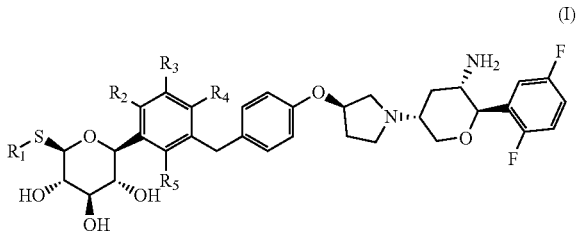

(I)

wherein, $R_1$ is $C_{1-3}$ alkyl, which is optionally substituted by 1, 2, or 3 $R_a$;

$R_2$ and $R_3$ are each independently selected from H, F, Cl, Br, I, OH, $NH_2$, $C_{1-3}$ alkyl, and $C_{1-3}$ alkoxy, wherein the $C_{1-3}$ alkyl and the $C_{1-3}$ alkoxy are optionally substituted by 1, 2, or 3 $R_b$;

$R_5$ is selected from H, F, Cl, Br, I, OH, $NH_2$, and $C_{1-3}$ alkyl, wherein the $C_{1-3}$ alkyl is optionally substituted by 1, 2, or 3 $R_c$;

$R_4$ is H, F, or Cl, and when $R_4$ is Cl, $R_2$, $R_3$, and $R_5$ are not H at the same time;

$R_a$, $R_b$ and $R_c$ are each independently selected from F, Cl, Br, I, OH, and $NH_2$.

The present disclosure also provides a compound of formula (I), an isomer thereof, or a pharmaceutically acceptable salt thereof,

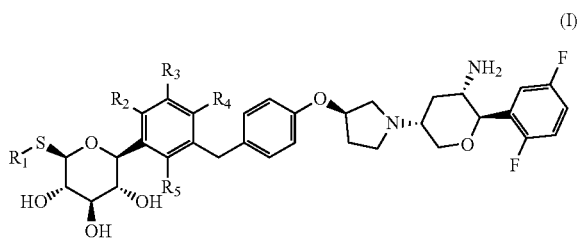

(I)

wherein, $R_1$ is $C_{1-3}$ alkyl, which is optionally substituted by 1, 2, or 3 $R_a$;

$R_2$ and $R_3$ are each independently selected from H, F, Cl, Br, I, OH, $NH_2$, and $C_{1-3}$ alkyl, wherein the $C_{1-3}$ alkyl is optionally substituted by 1, 2, or 3 $R_b$;

$R_5$ is selected from H, F, Cl, Br, I, OH, $NH_2$, and $C_{1-3}$ alkyl, wherein the $C_{1-3}$ alkyl is optionally substituted by 1, 2, or 3 $R_c$;

$R_4$ is H, F, or Cl, and when $R_4$ is Cl, $R_2$, $R_3$, and $R_5$ are not H at the same time;

$R_a$, $R_b$, and $R_c$ are each independently selected from F, Cl, Br, I, OH, and $NH_2$.

In some embodiments of the present disclosure, $R_1$ is $CH_3$, wherein the $CH_3$ is optionally substituted by 1, 2, or 3 $R_a$, and other variables are as defined in the present disclosure.

In some embodiments of the present disclosure, $R_1$ is $CH_3$, and other variables are as defined in the present disclosure.

In some embodiments of the present disclosure, $R_2$ and $R_3$ are each independently selected from H, F, Cl, Br, I, OH, $NH_2$, $CH_3$, Et, and —$OCH_3$, wherein the $CH_3$, Et, and —$OCH_3$ are optionally substituted by 1, 2, or 3 $R_b$, and other variables are as defined in the present disclosure.

In some embodiments of the present disclosure, $R_2$ and $R_3$ are each independently selected from H, F, Cl, Br, I, OH, $NH_2$, $CH_3$, and Et, wherein the $CH_3$ and Et are optionally substituted by 1, 2, or 3 $R_b$, and other variables are as defined in the present disclosure.

In some embodiments of the present disclosure, $R_2$ and $R_3$ are each independently selected from H, F, Cl, Br, I, OH, $NH_2$, $CH_3$, Et, and —$OCH_3$, and other variables are as defined in the present disclosure.

In some embodiments of the present disclosure, $R_2$ and $R_3$ are each independently selected from H, F, Cl, Br, I, OH, $NH_2$, $CH_3$, and Et, and other variables are as defined in the present disclosure.

In some embodiments of the present disclosure, $R_5$ is selected from H, F, Cl, Br, I, OH, $NH_2$, $CH_3$, and Et, wherein the $CH_3$ and Et are optionally substituted by 1, 2, or 3 $R_c$, and other variables are as defined in the present disclosure.

In some embodiments of the present disclosure, $R_5$ is selected from H, F, Cl, Br, I, OH, $NH_2$, $CH_3$, and Et, and other variables are as defined in the present disclosure.

Other embodiments of the present disclosure are derived from any combination of above variables.

The present disclosure also provides the following compounds, isomers thereof or pharmaceutically acceptable salts thereof,

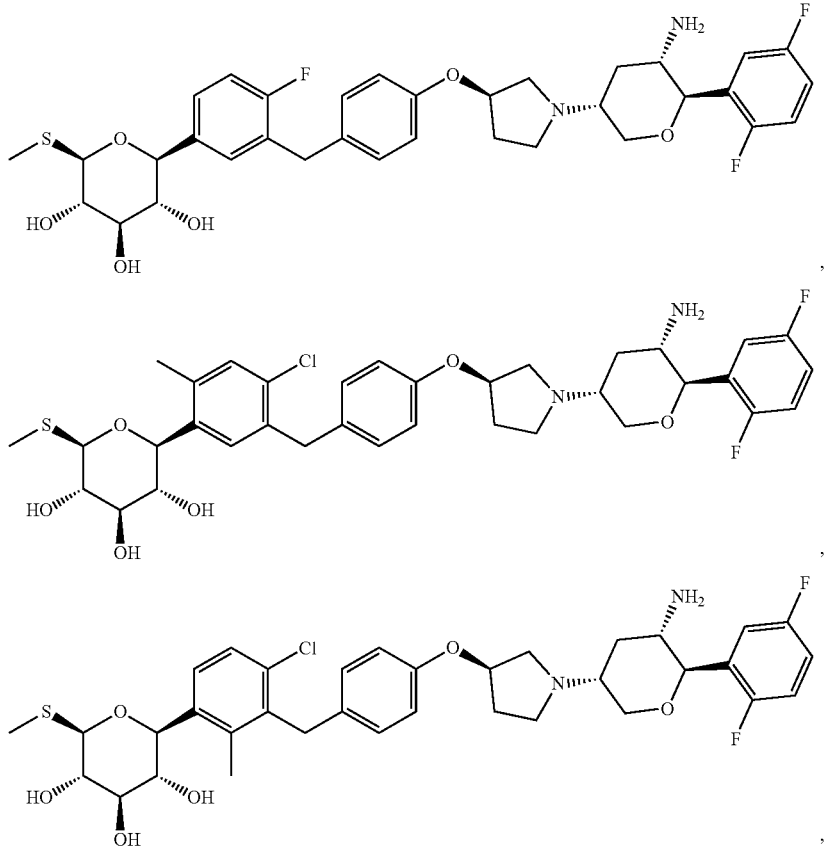

-continued

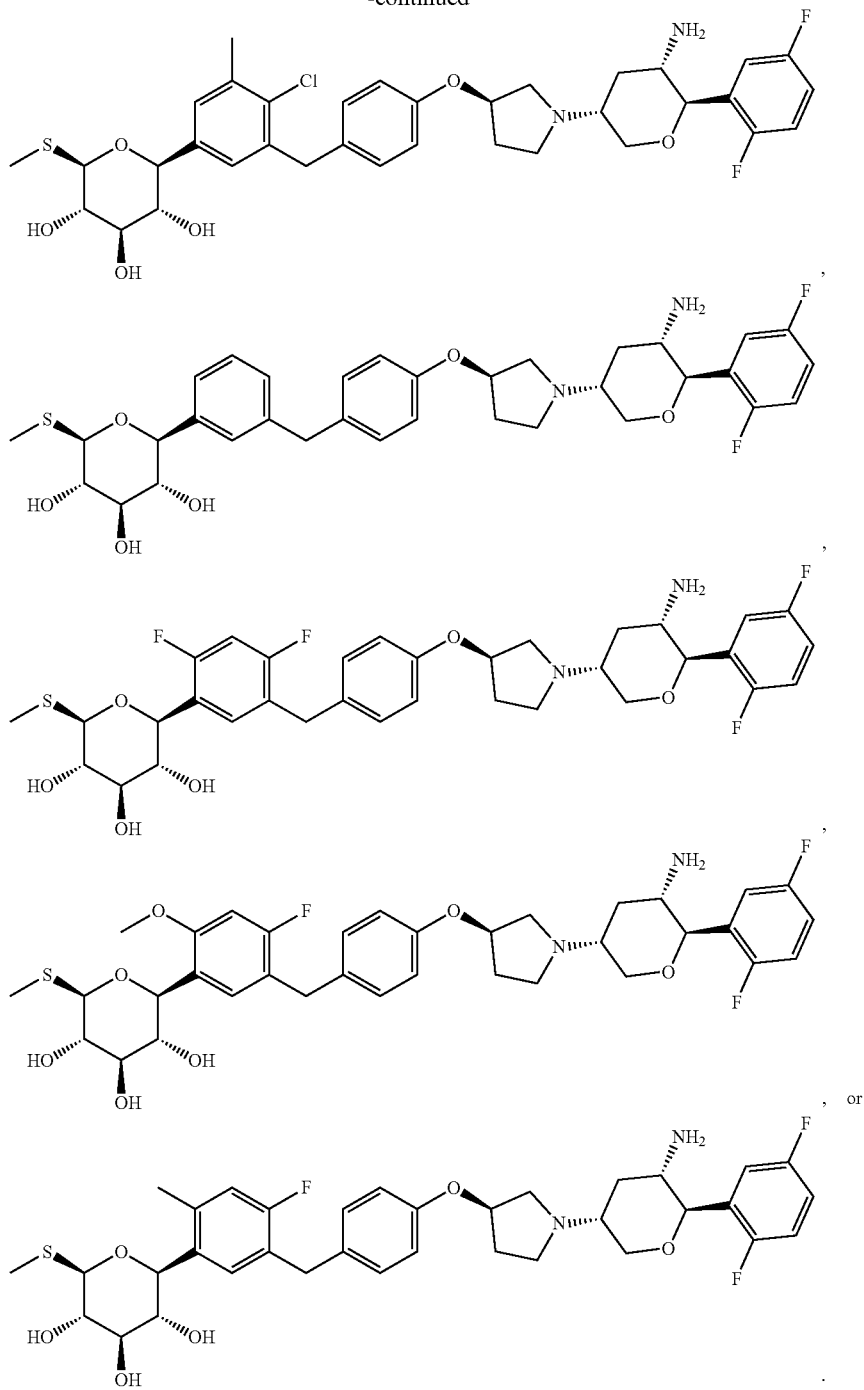

The present disclosure also provides a use of the above compound or the pharmaceutically acceptable salt thereof in the manufacture of a medicament as a SGLT2/DPP4 dual inhibitor.

TECHNICAL EFFECTS

The compounds of the present disclosure exhibit high selectivity for human SGLT2 and significant in vitro inhibitory activity against human SGLT2 and rhDPP4. The compounds of the present disclosure have good oral bioavailability, significant hypoglycemic effect, renal and hepatoprotective effects, and can be used in the treatment of diabetes and related metabolic disorder-derived diseases.

DEFINITION AND DESCRIPTION

Unless otherwise specified, the following terms and phrases when used herein have the following meanings. A specific term or phrase should not be considered indefinite or unclear in the absence of a particular definition, but should be understood in the ordinary sense. When a trading name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and or "(±)" refers to racemic.

Unless otherwise specified, the absolute configuration of a stereogenic center is represented by a wedged solid bond ( ◆ ) and a wedged dashed bond ( ◆ ), and the relative configuration of a stereogenic center is represented by a straight solid bond ( ◆ ) and a straight dashed bond ( ◆ ) a wave line ( ◆ ) is used to represent a wedged solid bond ( ◆ ) or a wedged dashed bond ( ◆ ) or the wave line ( ◆ ) is used to represent a straight solid bond ( ◆ ) and a straight dashed bond ( ◆ ).

Unless otherwise specified, when double bond structure, such as carbon-carbon double bond, carbon-nitrogen double bond, and nitrogen-nitrogen double bond, exists in the compound, and each of the atoms on the double bond is connected to two different substituents (including the condition where a double bond contains a nitrogen atom, the lone pair of electrons attached on the nitrogen atom is regarded as a substituent connected), if the atom on the double bond in the compound is connected to its substituent by a wave line ( ◆ ), this refers to the (Z) isomer, (E) isomer or a mixture of two isomers of the compound. For example, the following formula (A) means that the compound exists as a single isomer of formula (A-1) or formula (A-2) or as a mixture of two isomers of formula (A-1) and formula (A-2); the following formula (B) means that the compound exists in the form of a single isomer of formula (B-1) or formula (B-2) or in the form of a mixture of two isomers of formula (B-1) and formula (B-2). The following formula (C) means that the compound exists as a single isomer of formula (C-1) or formula (C-2) or as two a mixture of two isomers of formula (C-1) and formula (C-2).

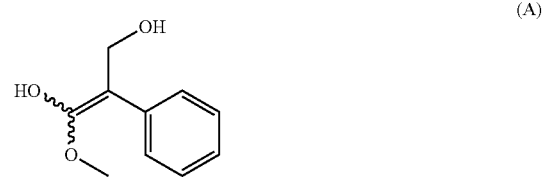

(A)

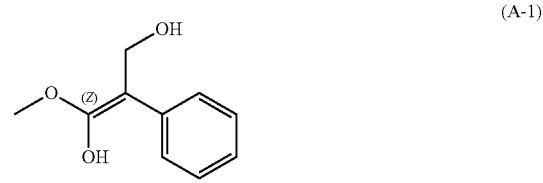

(A-1)

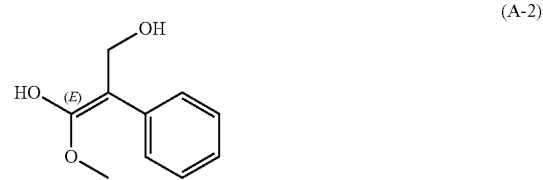

(A-2)

-continued

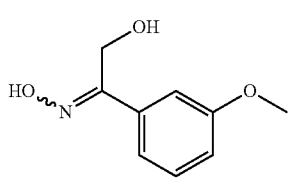
(B)

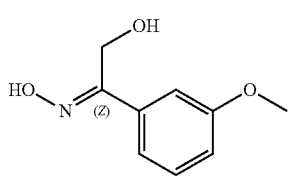
(B-1)

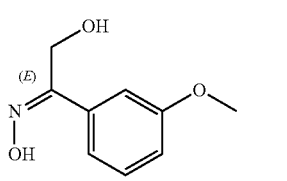
(B-2)

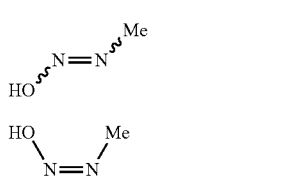
(C)

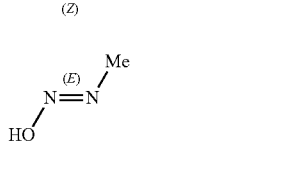
(C-1)

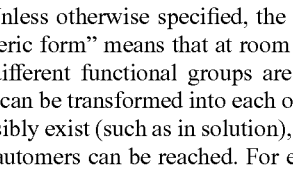
(C-2)

Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to obtain the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs and the like. All isotopic variations of the compound of the present disclosure, whether radioactive or not, are encompassed within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as is chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

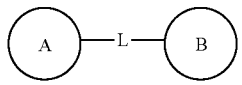

is -M-W—, then -M-W— can link ring A and ring B to form

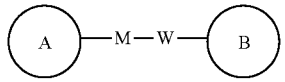

in the direction same as left-to-right reading order, and form

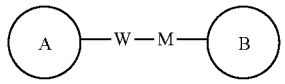

in the direction contrary to left-to-right reading order. A combination of the linking groups, substituents and/or variables thereof is allowed only when such combination can result in a stable compound.

Unless otherwise specified, when a group has one or more linkable sites, any one or more of the sites of that group may be linked to other groups by chemical bonding. The chemical bond between the site and other groups can be represented by a straight solid bond ( ╱ ), a straight dashed bond ( ╱ ) or a wavy line ( ～ ). For example, the straight solid bond in —OCH₃ means that it is linked to other groups through the oxygen atom in the group; the straight dashed bonds in

means that it is linked to other groups through the two ends of nitrogen atom in the group; the wave lines in

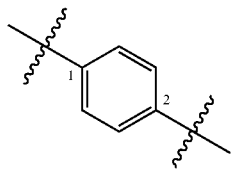 [SMILES: *c1ccc(*)cc1]

means that the phenyl group is linked to other groups through carbon atoms at position 1 and position 2.

Unless otherwise specified, the term "$C_{1-3}$ alkyl" refers to a linear or branched saturated hydrocarbon group having 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl) and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like; similarly, n membered to n+m membered means that the number of atoms on the ring is from n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring and the like.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy and the like. Examples of $C_{1-3}$ alkoxy include, but are not limited to, methoxy, ethoxy, propoxy (including n-propoxy and isopropoxy) and the like.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The present disclosure uses the following abbreviations: aq refers to water; HATU refers to O-(7-azabenzotriazol-1-yl)-N,N,N',N'-tetramethyluronium hexafluorophosphate; EDC refers to N-(3-dimethylaminopropyl)-N'-ethylcarbodiimide hydrochloride; m-CPBA refers to 3-chloroperoxybenzoic acid; eq refers to equivalent, equivalents; CDI refers to carbonyl diimidazole; DCM refers to dichloromethane; PE refers to petroleum ether; DIAD refers to diisopropyl azo dicarboxylate; DMF refers to N,N-dimethylformamide; DMSO refers to dimethyl sulfoxide; EtOAc refers to ethyl acetate; EtOH refers to ethanol; MeOH refers to methanol; CBz refers to benzyloxycarbonyl, an amine protecting group; BOC refers to tert-butoxycarbonyl, an amine protecting group; HOAc refers to acetic acid; NaCNBH$_3$ refers to sodium cyanoborohydride; r.t. refers to room temperature; O/N refers to overnight; THF refers to tetrahydrofuran; Boc$_2$O refers to di-tert-butyldicarbonate; TFA refers to trifluoroacetic acid; DIPEA refers to diisopropylethylamine; SOCl$_2$ refers to sulfoxide chloride; CS$_2$ refers to carbon disulfide; TsOH refers to p-toluenesulfonic acid; NFSI refers to N-fluorobenzenesulfonimide; n-Bu$_4$NF refers to tetrabutylammonium fluoride; iPrOH refers to 2-propanol; mp refers to melting point; LDA refers to lithium diisopropylamine; Et refers to ethyl.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

Figure 1:
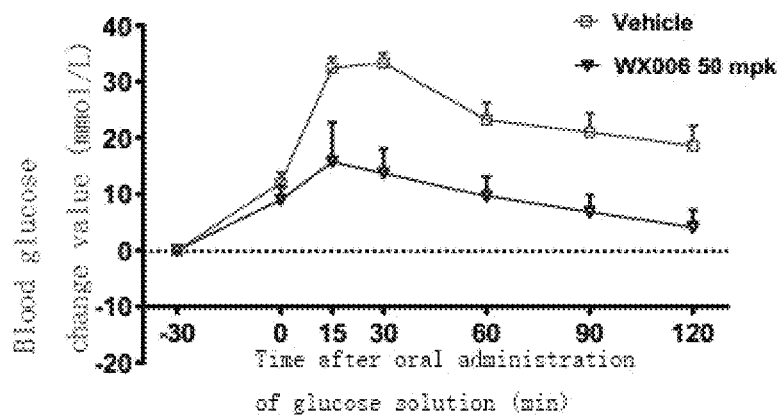
FIG. 1 is the blood glucose change value-time curve.
Figure 2:
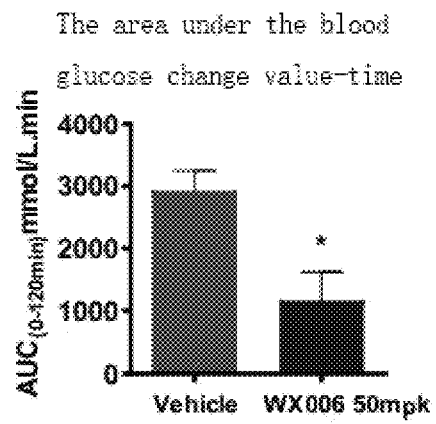
FIG. 2 is the area under the blood glucose change value-time curve.
Figure 3:
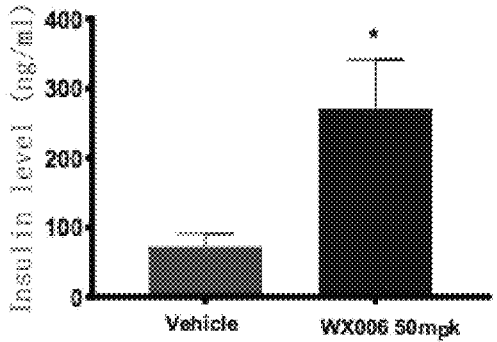
FIG. 3 is the insulin level in plasma at 1 hour of glucose administration.
Figure 4:
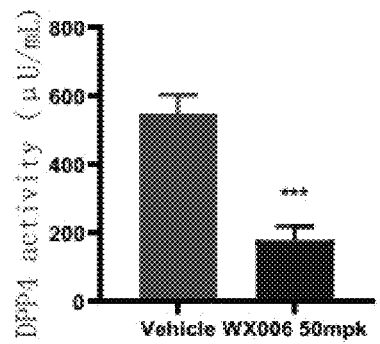
FIG. 4 is the DPP4 activity in plasma at 2 hours of glucose administration.
Figure 5:
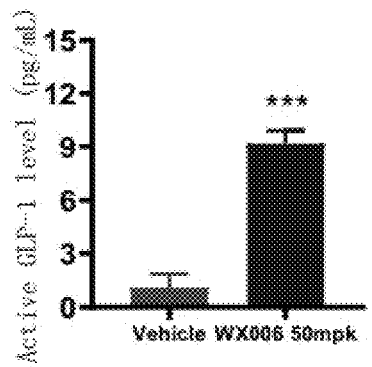
FIG. 5 is the level of active GLP-1 in plasma at 2 hours of glucose administration.

The present disclosure is described in detail by the embodiments below, but it does not mean that there are any adverse restrictions on the present disclosure. The present disclosure has been described in detail herein, wherein specific embodiments thereof are also disclosed, and it will be apparent to those skilled in the art that various variations and improvements can be made to specific embodiments of the present disclosure without departing from the spirit and scope of the present disclosure.

Reference Embodiment 1: Fragment A-1

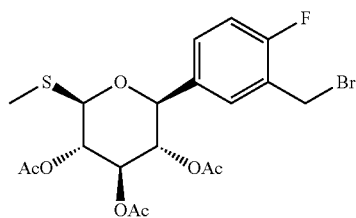 [SMILES: CS[C@H]1O[C@@H](c2ccc(F)c(CBr)c2)[C@H](OC(C)=O)[C@@H](OC(C)=O)[C@@H]1OC(C)=O]

Synthetic Route

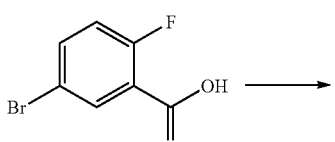

A-1-1

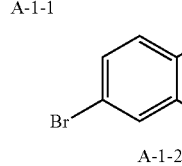

A-1-2

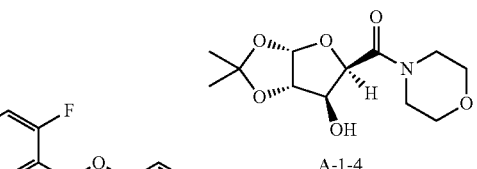

A-1-3

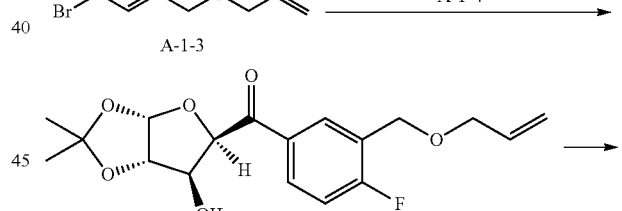

A-1-5

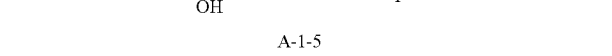

A-1-6

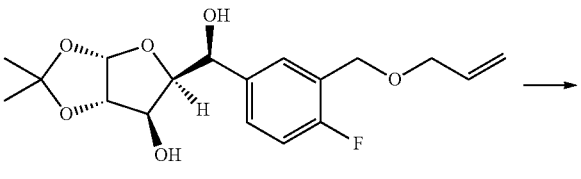

A-1-7

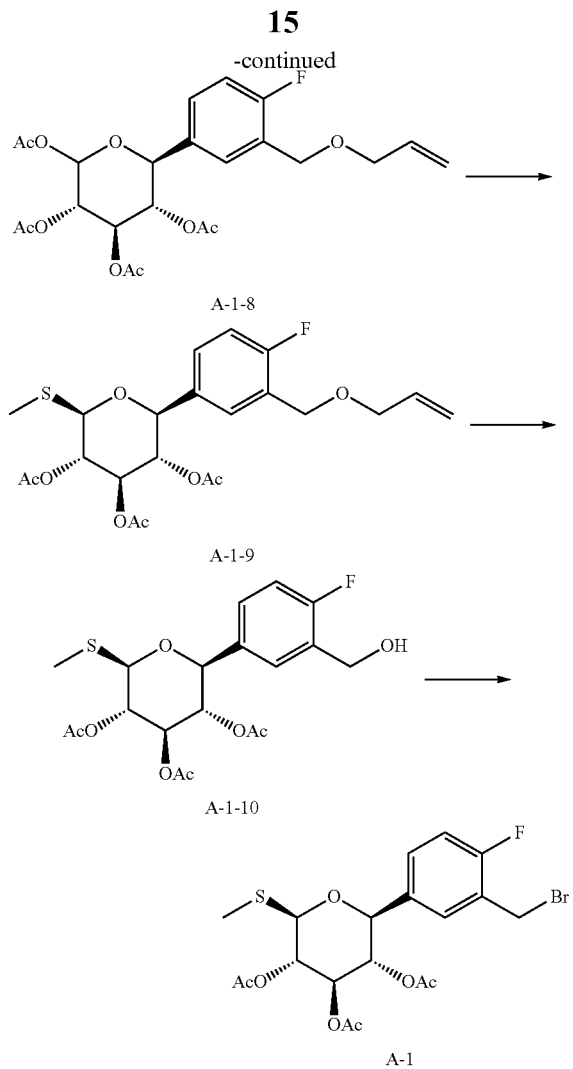

A-1-8

A-1-9

A-1-10

A-1

Step 1: Synthesis of Compound A-1-2

Compound A-1-1 (20 g, 91.32 mmol) was added to a reaction flask containing anhydrous tetrahydrofuran (100 mL). After addition dropwise with a solution of borane in tetrahydrofuran (1 M, 120 mL) into the reaction under nitrogen protection, the mixture was stirred at 15° C. for 16 hours. After the reaction was completed, the reaction was quenched by dropwise with methanol (70 mL) under nitrogen protection. The mixture was concentrated under reduced pressure to obtain a crude product of compound A-1-2, which was directly used in the next reaction step. MS m/z: 229.7 [M+23]$^+$.

Step 2: Synthesis of Compound A-1-3

Compound A-1-2 (19 g, 92.31 mmol, crude product) was added to a reaction flask containing anhydrous N,N-dimethylformamide (100 mL). After the mixture was cooled to 0° C., sodium hydride (7.00 g, 174.88 mmol) was added to the reaction and the mixture was stirred for 0.5 hours. After the reaction was slowly warmed up to 15° C., allyl bromide (34 g, 281.04 mmol) was added to the reaction and the mixture was continuously stirred for 18 hours. After the reaction was completed, the reaction solution was quenched by dropwise with saturated ammonium chloride aqueous solution (50 mL), the mixture was concentrated under reduced pressure to obtain the residue as a yellow viscous material. Dichloromethane (200 mL) and water (200 mL) were added to the residue and stirred. The organic phase was separated and washed with water (100 mL*2), concentrated under reduced pressure to obtain a crude product. The crude product was purified by column chromatography (petroleum ether 100% system) to obtain compound A-1-3.

Step 3: Synthesis of Compound A-1-5

A solution of n-butyllithium in n-hexane (2.5 M, 33.00 mL) was added dropwise to a solution of compound A-1-3 (15.00 g, 61.20 mmol) in anhydrous tetrahydrofuran (150 mL) at −70° C. under nitrogen protection. After the addition was completed, the reaction was stirred at −70° C. for 0.5 hours to prepare reaction system A. A solution of tert-butylmagnesium chloride in tetrahydrofuran (1.7 M, 69.00 mL) was added dropwise to a solution of compound A-1-4 (16.73 g, 61.20 mmol) in anhydrous tetrahydrofuran (150 mL) at 0° C. under nitrogen protection. After the addition was completed, the reaction was stirred at 0° C. for 0.5 hours and then the mixture was added dropwise to the reaction system A. After the addition was completed, the reaction was stirred at −70° C. for 0.5 hours. The reaction was slowly warmed up to 20° C. and continuously stirred for 2 hours. After the reaction was completed, the mixture was added dropwise with saturated ammonium chloride aqueous solution (100 mL) to quench the reaction, the mixture was concentrated to remove the organic solvent, and the residue was extracted with ethyl acetate (100 mL*3), the organic phases were combined and washed with saturated brine (100 mL), dried over anhydrous sodium sulfate, and filtered, then the filtrate was concentrated to obtain a crude product. The crude product was purified by column chromatography (petroleum ether/ethyl acetate=10:1 to 1:1) to obtain compound A-1-5. $^1$H NMR (400 MHz, CHCl$_3$-d) δ ppm 1.37 (s, 3H) 1.58 (s, 3H) 3.07 (d, J=4.27 Hz, 1H) 4.06-4.11 (m, 2H) 4.59-4.68 (m, 4H) 5.24 (dd, J=10.42, 1.38 Hz, 1H) 5.30-5.33 (m, 1H) 5.35 (dd, J=17.32, 1.51 Hz, 1H) 5.90-6.03 (m, 1H) 6.10 (d, J=3.51 Hz, 1H) 7.15 (t, J=9.03 Hz, 1H) 8.05 (ddd, J=8.22, 5.33, 2.26 Hz, 1H) 8.20 (dd, J=6.90, 2.13 Hz, 1H).

Step 4: Synthesis of Compound A-1-6

Sodium borohydride (1.20 g, 31.72 mmol) was slowly added in batches into a mixture of Compound A-1-5 (6.20 g, 13.72 mmol), cerium trichloride heptahydrate (6.20 g, 16.64 mmol, 1.58 mL) in anhydrous methanol (100 mL) at 0° C. After addition completed, the reaction was stirred at 20° C. for 16 hours. After the reaction was completed, the reaction was quenched by adding dropwise with saturated ammonium chloride solution (100 mL). The mixture was concentrated to remove the organic solvent, and the mixture became turbid. Citric acid was added to the mixture and adjust the mixture to clarify; then the mixture was extracted with ethyl acetate (100 mL*3), The organic phases were separated and combined, washed with saturated brine (100 mL), dried over anhydrous sodium sulfate, and filtered, then the filtrate was concentrated to obtain a crude product of compound A-1-6, which was directly used in the next reaction step. MS m/z: 372.0 [M+18]$^+$.

Step 5: Synthesis of Compound A-1-7

A mixture of Compound A-1-6 (8.00 g, 17.60 mmol) in acetic acid (42.00 g, 699.42 mmol, 40 mL) and water (40 mL) was stirred at 100° C. for 6 hours. After the reaction was completed, the mixture was concentrated to obtain the crude product as a yellow solid. The crude product was added with toluene (30 mL), and concentrated again. This operation was repeat twice to obtain a crude product of compound A-1-7, which was directly used in the next reaction step. MS m/z: 331.9 [M+18]$^+$.

Step 6: Synthesis of Compound A-1-8

To a mixture of Compound A-1-7 (8.00 g, 17.94 mmol), triethylamine (13.81 g, 136.51 mmol, 19.0 mL) in acetonitrile (100 mL) was added acetic anhydride (16.35 g, 160.16 mmol, 15.0 mL), followed by 4-dimethylaminopyridine (35 mg, 286.49 µmol). The reaction was stirred at 20° C. for 8 hours. After the reaction was completed, the reaction was quenched by adding dropwise with saturated sodium bisulfate aqueous solution (10 mL), the mixture was added with water (100 mL) and ethyl acetate (100 mL). The mixture was stirred and then the organic phase was separated; the aqueous phase was extracted twice with ethyl acetate (100 mL). The organic phases were combined, and washed with saturated brine (100 mL), dried over anhydrous sodium sulfate, and filtered, then the filtrate was concentrated to obtain a crude product. The crude product was purified by column chromatography (petroleum ether/ethyl acetate=10:1 to 2:1) to obtain compound A-1-8. MS m/z: 500.1 [M+18]$^+$.

Step 7: Synthesis of Compound A-1-9

To a mixture of Compound A-1-8 (4.00 g, 6.50 mmol) in anhydrous dioxane (50 mL) were added with thiourea (1.28 g, 16.82 mmol), followed by trimethylsilyl trifluoromethanesulfonate (4.92 g, 22.14 mmol, 4.00 mL) under nitrogen protection. The reaction was stirred at 80° C. for 2 hours. After detecting the formation of intermediate, the reaction was cooled down to 20° C., and iodomethane (3.60 g, 25.36 mmol, 1.58 mL) and diisopropylethylamine (4.20 g, 32.48 mmol, 5.66 mL) were added, and the reaction was stirred at 20° C. for 16 hours. The reaction was quenched by adding with methanol (10 mL), then the mixture was concentrated under reduced pressure. The residue was added with water (50 mL) and the mixture was extracted with ethyl acetate (50 mL*3). The organic phases were combined, washed with saturated brine (50 mL), dried over anhydrous sodium sulfate, and filtered, then the filtrate was concentrated under reduced pressure to obtain a crude product. The crude product was purified by column chromatography (petroleum ether/ethyl acetate=10:1 to 3:1) to obtain compound A-1-9. MS m/z: 493.0 [M+23]$^+$.

Step 8: Synthesis of Compound A-1-10

To a mixture of Compound A-1-9 (3.20 g, 5.80 mmol), barbituric acid dihydrate (1.50 g, 11.68 mmol, 2.01 eq) in anhydrous ethanol (40 mL) were added with tetrakis(triphenylphosphine) palladium (0.32 g, 276.92 µmol, 5% mol eq) under nitrogen protection and the reaction was stirred at 40° C. for 14 hours. After the reaction was completed, the reaction mixture was cooled and filtered, and the filtrate was concentrated under reduced pressure. The residue was added with water (50 mL) and the mixture was extracted with ethyl acetate (50 mL*3). The organic phases were combined and washed with saturated brine (50 mL), dried over anhydrous sodium sulfate, and filtered, then the filtrate was concentrated under reduced pressure to obtain a crude product. The crude product was purified by column chromatography (petroleum ether/ethyl acetate=10:1 to 1:1) to obtain compound A-1-10. $^1$H NMR (400 MHz, CDCl$_3$) δ ppm 7.46 (dd, J=7.03, 2.01 Hz, 1H) 7.23-7.27 (m, 1H) 6.97-7.11 (m, 1H) 5.32-5.43 (m, 1H) 5.17-5.28 (m, 1H) 5.12 (t, J=9.66 Hz, 1H) 4.76 (br d, J=5.27 Hz, 2H) 4.55 (d, J=9.79 Hz, 1H) 4.45 (d, J=9.79 Hz, 1H) 2.20 (s, 3H) 2.10 (s, 3H) 2.02 (s, 3H) 1.83 (s, 3H) 1.80-1.86 (m, 1H).

Step 9: Synthesis of Compound A-1

Phosphorus tribromide (34.59 mg, 127.78 µmol, 12.14 µL) was added dropwise to a solution of compound A-1-10 (0.11 g, 255.55 µmol) in anhydrous tetrahydrofuran (2 mL) under nitrogen protection at 0° C. The reaction was stirred for 16 hours, the temperature was increased from 0° C. to 20° C. during this period. After the reaction was completed, an aqueous solution of potassium carbonate (2 M, 5.5 mL) was added slowly to the reaction and stirring for 10 min to quench the reaction. The reaction solution was stratified after standing and the aqueous phase was extracted with ethyl acetate (10 mL*2), then the organic phases were combined, washed with water (20 mL) and saturated brine (10 mL) sequentially, dried over anhydrous sodium sulfate and concentrated under reduced pressure to obtain a crude product. The crude product was stirred with n-hexane (10 mL) for 1 hour at room temperature. The solid was collected by filtration and washed with n-hexane (2 mL×3), and the filter cake was concentrated under reduced pressure to remove the residual solvent to obtain compound A-1. $^1$H NMR (400 MHz, CDCl$_3$) δ 7.39-7.30 (m, 2H), 7.09-7.03 (m, 1H), 5.36 (t, J=9.6 Hz, 1H), 5.22 (t, J=9.6 Hz, 1H), 5.07 (t, J=9.6 Hz, 1H), 4.58-4.52 (m, 2H), 4.48-4.41 (m, 2H), 2.21 (s, 3H), 2.11 (s, 3H), 2.02 (s, 3H), 1.86 (s, 3H).

Each fragment A-2, A-3, A-4, A-5 in Table 1 was synthesized by referring to synthesis methods of steps 1 to 9 in Reference embodiment 1.

TABLE 1

| Reference embodiment | Fragment | Structure | NMR |
|---|---|---|---|
| 2 | A-2 | 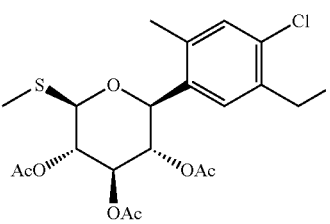 | $^1$H NMR (400 MHz, CDCl$_3$) δ ppm 1.69-1.78 (m, 3 H) 1.83 (s, 3 H) 1.94-2.01 (m, 2 H) 2.03 (s, 3 H) 2.11 (s, 3 H) 2.20 (s, 3 H) 2.40 (s, 3 H) 3.47 (t, J = 6.78 Hz, 3 H) 3.71 (t, J = 6.40 Hz, 2 H) 4.50-4.59 (m, 3 H) 4.66 (d, J = 10.04 Hz, 1 H) 5.20-5.40 (m, 3 H) 7.20 (s, 1 H) 7.41 (s, 1 H). |

TABLE 1-continued
| Reference embodiment | Fragment | Structure | NMR |
|---|---|---|---|
| 3 | A-3 | 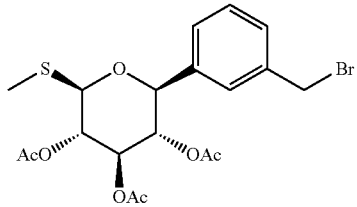 | $^1$H NMR (400 MHz, CDCl$_3$) δ ppm 1.85 (s, 3H), 2.04 (s, 3H), 2.13 (s, 3H), 2.21 (s, 3H), 2.48 (s, 3H), 4.58 (d, J = 10.01 Hz, 1H), 4.66 (d, J = 10.38 Hz, 1H), 4.72-4.83 (m, 2H), 5.23 (td, J = 9.60, 7.82 Hz, 2H), 5.37-5.44 (m, 1H), 7.29-7.37 (m, 2H). |
| 4 | A-4 | 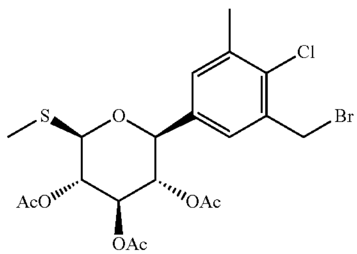 [SMILES: CS[C@H]1O[C@@H](c2cc(C)c(Cl)c(CBr)c2)[C@H](OC(C)=O)[C@@H](OC(C)=O)[C@@H]1OC(C)=O] | $^1$H NMR (400 MHz, CDCl$_3$) δ ppm 1.86 (s, 3H), 2.01 (s, 3H), 2.10 (s, 3H), 2.21 (s, 3H), 2.40 (s, 3H), 4.40 (d, J = 10.04 Hz, 1H), 4.51-4.57 (m, 2H), 4.60-4.65 (m, 1H), 5.06 (t, J = 9.66 Hz, 1H), 5.17-5.25 (m, 1H), 5.31-5.38 (m, 1H), 7.22 (s, 1H), 7.24 (s, 1H). |
| 5 | A-5 | 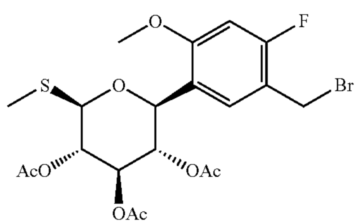 [SMILES: COc1cc(F)c(CBr)cc1[C@@H]1O[C@H](SC)[C@@H](OC(C)=O)[C@H](OC(C)=O)[C@H]1OC(C)=O] | $^1$H NMR (400 MHz, CDCl$_3$) δ ppm 1.82 (s, 3H), 2.04 (s, 3H), 2.12 (s, 3H), 2.21 (s, 3H), 3.86 (s, 3H), 4.44-4.58 (m, 3H), 4.86 (br d, J = 9.29 Hz, 1H), 5.22 (t, J = 9.54 Hz, 1H), 5.31-5.42 (m, 2H), 6.61 (d, J = 11.54 Hz, 1H), 7.38 (d, J = 8.28 Hz, 1H) |
Reference Embodiment 6: Fragment A-6
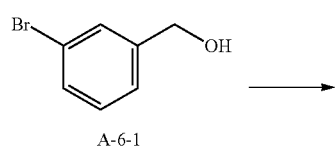
Synthetic Route
A-6-1
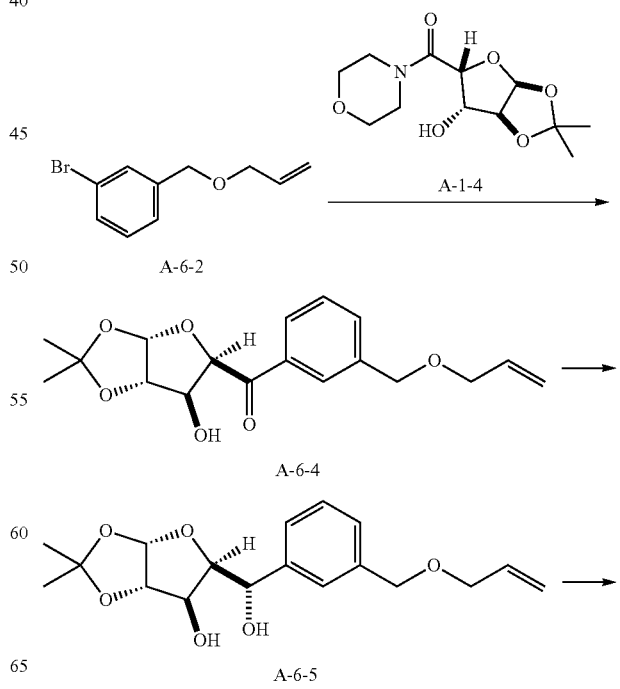
A-6-2
A-6-4
A-6-5

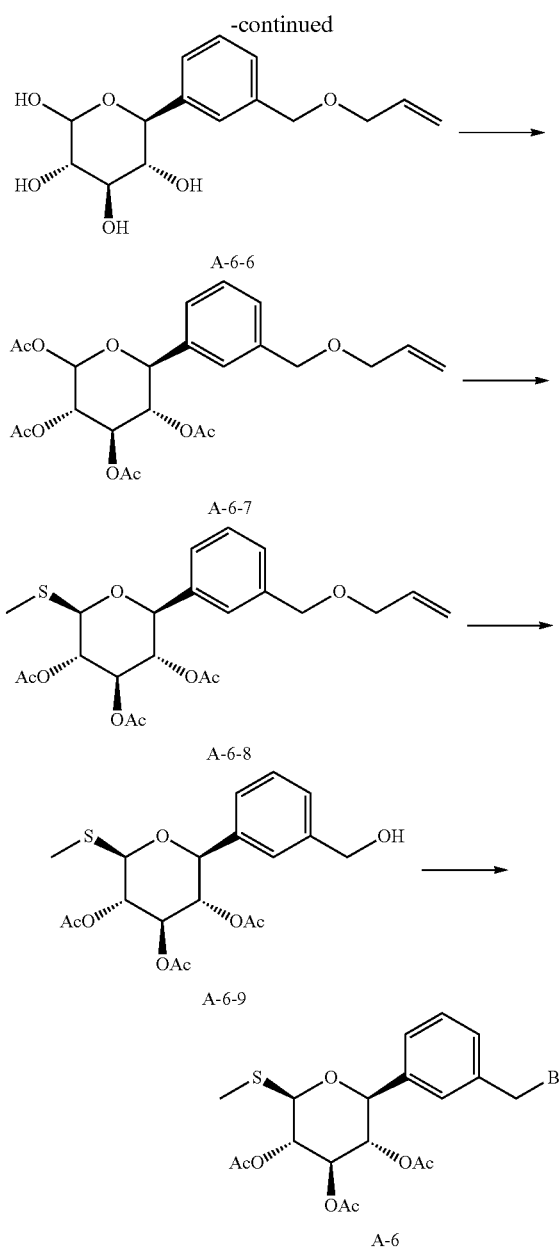

1.4 Hz, 2H), 4.45-4.52 (m, 2H), 5.17-5.34 (m, 2H), 5.95 (ddt, J=17.2, 10.7, 5.5, 5.5 Hz, 1H), 7.22-7.32 (m, 2H), 7.43 (d, J=7.5 Hz, 1H), 7.51 (s, 1H).

Step 2: Synthesis of Compound A-6-4

A solution of n-Butyllithium (2.5 M, 27.12 mL, 1.1 eq) was added dropwise to a solution of compound A-6-2 (14 g, 61.65 mmol, 1 eq) in anhydrous tetrahydrofuran (140 mL) at −78° C. under nitrogen protection. After the dropwise addition was completed, the reaction was stirred at −78° C. for 0.5 hours to obtain reaction system A. A solution of tert-butylmagnesium chloride (1.7 M, 47.14 mL, 1.3 eq) was added dropwise to a solution of compound A-1-4 (18.53 g, 67.81 mmol, 1.1 eq) in anhydrous tetrahydrofuran (180 mL) under nitrogen protection at 0° C. After the dropwise addition was completed, the reaction was stirred at 0° C. for 0.5 hours to prepare reaction system B. The reaction system B was slowly added to the reaction system A at −78° C. under nitrogen protection. The reaction was carried out at −78° C. for 0.5 hours, then the mixture was warmed up to 25° C. and stirred for 15.5 hours. After the reaction was completed, the reaction was quenched by adding an aqueous solution of ammonium chloride (100 mL) to the reaction at 0° C., and the mixture was diluted by ethyl acetate (200 mL). The organic phase was separated and washed with water (50 mL*2), followed by saturated brine (50 mL*2), dried over anhydrous sodium sulfate and concentrated under reduced pressure, then the residue was purified by column chromatography (petroleum ether:ethyl acetate=4:1) to obtain target compound A-6-4, which was confirmed by LCMS, LC-MS (m/z) 357 [M+Na]⁺.

Step 3: Synthesis of Compound A-6-5

Compound A-6-4 (13 g, 38.88 mmol, 1 eq) was dissolved in methanol (130 mL) and the mixture was cooled to 0° C. Cerium trichloride (9.58 g, 38.88 mmol, 2.44 mL, 1 eq) and sodium borohydride (2.94 g, 77.76 mmol, 2 eq) were added to the mixture sequentially, the mixture was warmed up to 25° C. and reacted for 16 hours. After the reaction was completed, the reaction was quenched by saturated ammonium chloride aqueous solution (30 mL). The mixture was concentrated under reduced pressure, and the residue was added with ethyl acetate (100 mL) and washed with water (50 mL*2). The organic phase was separated and washed with saturated brine (50 mL*2), dried over anhydrous sodium sulfate, filtered and concentrated under reduced pressure to obtain target compound A-6-5, which was confirmed by LCMS, LC-MS (m/z) 359 [M+Na]⁺.

Step 4: Synthesis of Compound A-6-6

Compound A-6-5 (10.8 g, 32.11 mmol, 1 eq) was dissolved in a solvent of water (50 mL) and glacial acetic acid (50 mL) and the reaction was reacted at 100° C. for 16 hours. After the reaction was completed, the mixture was concentrated under reduced pressure, and the residue was added with toluene (150 mL) and concentrated under reduced pressure again to obtain compound A-6-6, which was confirmed by LCMS, LC-MS (m/z) 319 [M+Na]⁺.

Step 5: Synthesis of Compound A-6-7

Compound A-6-6 (9.2 g, 31.05 mmol, 1 eq) was dissolved in 1,4-dioxane (100 mL), and then the reaction was added with acetic anhydride (25.36 g, 248.38 mmol, 23.26 mL, 8

Step 1: Synthesis of Compound A-6-2

Compound A-6-1 (25 g, 133.67 mmol, 1 eq) was dissolved in tetrahydrofuran (250 mL), and sodium hydride (10.69 g, 267.33 mmol, 2 eq) was added at 0° C., the reaction was warmed up to 25° C. and stirred for 0.5 hours. Allyl bromide (48.51 g, 401.00 mmol, 34.65 mL, 3 eq) was added slowly to the reaction and the reaction was continued stirred at 25° C. for 1.5 hours after addition. After the reaction was completed, the reaction was quenched by adding saturated ammonium chloride aqueous solution (100 mL) at 0° C., and the mixture was extracted with ethyl acetate (250 mL×2). The organic phases were combined and concentrated under reduced pressure to obtain a crude product. The crude product was purified by column chromatography (petroleum ether) to obtain target compound A-6-2. ¹H NMR (400 MHz, CD₃OD) δ ppm 4.04 (dt, J=5.5, eq), pyridine (24.56 g, 310.48 mmol, 25.06 mL, 10 eq), and 4-dimethylaminopyridine (1.90 g, 15.52 mmol, 0.5 eq). The mixture was stirred at 80° C. for 16 hours. After the reaction was completed, the mixture was concentrated under reduced pressure and the residue was diluted with ethyl acetate (100 mL). The organic phase was washed with 1 M hydrochloric acid (100 mL*4), water (50 mL*2), and saturated brine (50 mL*2) sequentially. The organic phase was dried over anhydrous sodium sulfate, filtered and concentrated under reduced pressure to get the residue. The residue was purified by column chromatography (petroleum ether:ethyl acetate=3:1) to obtain target compound A-6-7, which was confirmed by LCMS, LC-MS (m/z) 487 [M+Na]⁺.

Step 6: Synthesis of A-6-8

To a solution of Compound A-6-7 (6.2 g, 13.35 mmol, 1 eq) in 1,4-dioxane (62 mL) was added thiourea (3.56 g, 46.72 mmol, 3.5 eq), followed by trimethylsilyl trifluoromethanesulfonate (11.87 g, 53.40 mmol, 4 eq) at 25° C. under nitrogen protection. The reaction was warmed up to 60° C. and reacted for 1 hour, then cooled to 25° C., and added with iodomethane (9.47 g, 66.74 mmol, 5 eq) and diisopropylethylamine (17.25 g, 133.49 mmol, 10 eq) sequentially. The reaction was continuously stirred at 25° C. for 15 hours after addition. After the reaction was completed, the reaction was quenched by water (60 mL), extracted with ethyl acetate (60 mL*3), and the organic phases were combined, washed with saturated brine (50 mL), dried over anhydrous sodium sulfate and concentrated under reduced pressure. The residue was purified by column chromatography (petroleum ether:ethyl acetate=4:1) to obtain the target compound A-6-8, which was confirmed by LCMS, LC-MS (m/z) 475 [M+Na]⁺.

Step 7: Synthesis of A-6-9

A mixture of A-6-8 (4.4 g, 9.72 mmol, 1 eq), barbituric acid (2.49 g, 19.45 mmol, 2 eq) in ethanol (44 mL) was added with tetrakis(triphenylphosphine)palladium (516.80 mg, 486.17 μmol, 0.05 eq) under nitrogen protection. The reaction was stirred at 65° C. for 16 hours. After the reaction was completed, the pH of the mixture was adjusted to 7 to 8 by aqueous solution of saturated sodium bicarbonate. The mixture was filtered, and the filtrate was extracted with ethyl acetate (40 mL*2). The combined organic phases were washed with saturated brine (20 mL), dried over anhydrous sodium sulfate and concentrated under reduced pressure to obtain a crude product. The crude product was purified by column chromatography (petroleum ether:ethyl acetate=3:2) to obtain target compound A-6-9, which was confirmed by LCMS, LC-MS (m/z) 435 [M+Na]⁺.

Step 8: Synthesis of A-6

Phosphorus tribromide (98.44 mg, 363.68 μmol, 34.18 μL, 0.5 eq) was added to a solution of compound A-6-9 (300 mg, 727.36 μmol, 1 eq) in anhydrous tetrahydrofuran (3 mL) under nitrogen protection at 0° C., and the reaction was stirred at 0° C. for 3 hours. After the reaction was completed, the reaction solution was washed with 1 N potassium carbonate aqueous solution, and the organic phase was separated, and the aqueous phase was extracted with dichloromethane (2 mL). The organic phases were combined and concentrated under reduced pressure to get the crude product. The crude product was purified by column chromatography (petroleum ether:ethyl acetate=4:1) to obtain target compound A-6. ¹H NMR (400 MHz, CDCl₃) δ ppm 1.83-1.86 (m, 3H), 2.02 (s, 3H), 2.10-2.13 (m, 3H), 2.20-2.22 (m, 3H), 4.46-4.49 (m, 2H), 4.54-4.58 (m, 1H), 5.10 (t, J=9.7 Hz, 1H), 5.20-5.27 (m, 1H), 5.31 (s, 1H), 5.34-5.40 (m, 1H), 7.30-7.38 (m, 4H).

Reference Embodiment 7: Fragment a-7

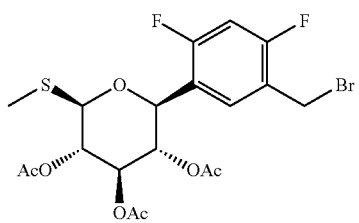 [SMILES: CS[C@H]1O[C@@H](c2cc(CBr)c(F)cc2F)[C@H](OC(C)=O)[C@@H](OC(C)=O)[C@@H]1OC(C)=O]

Synthetic Route

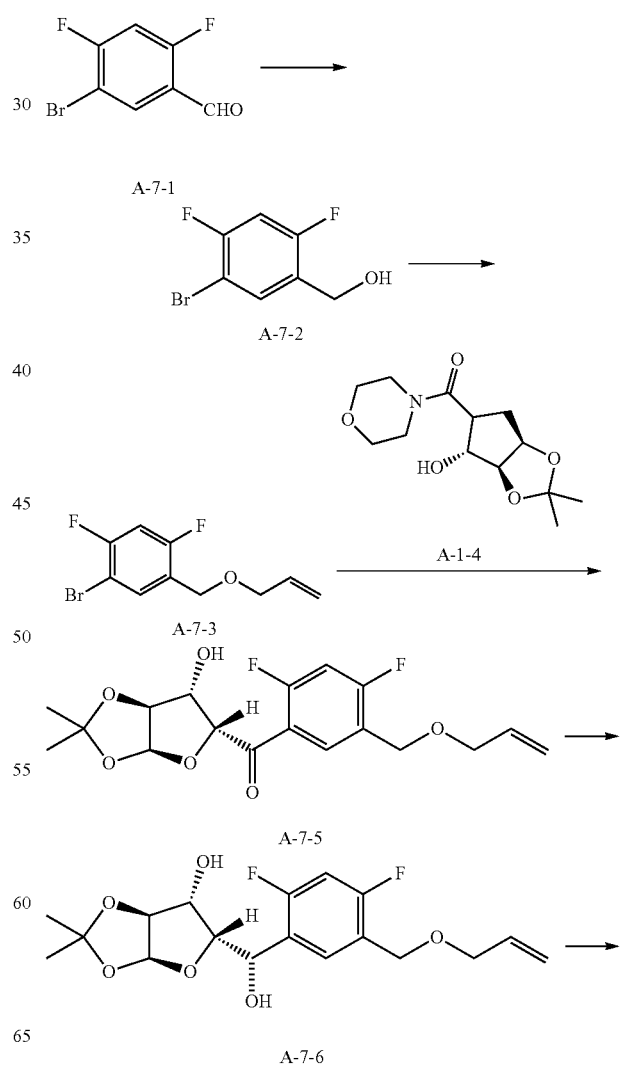

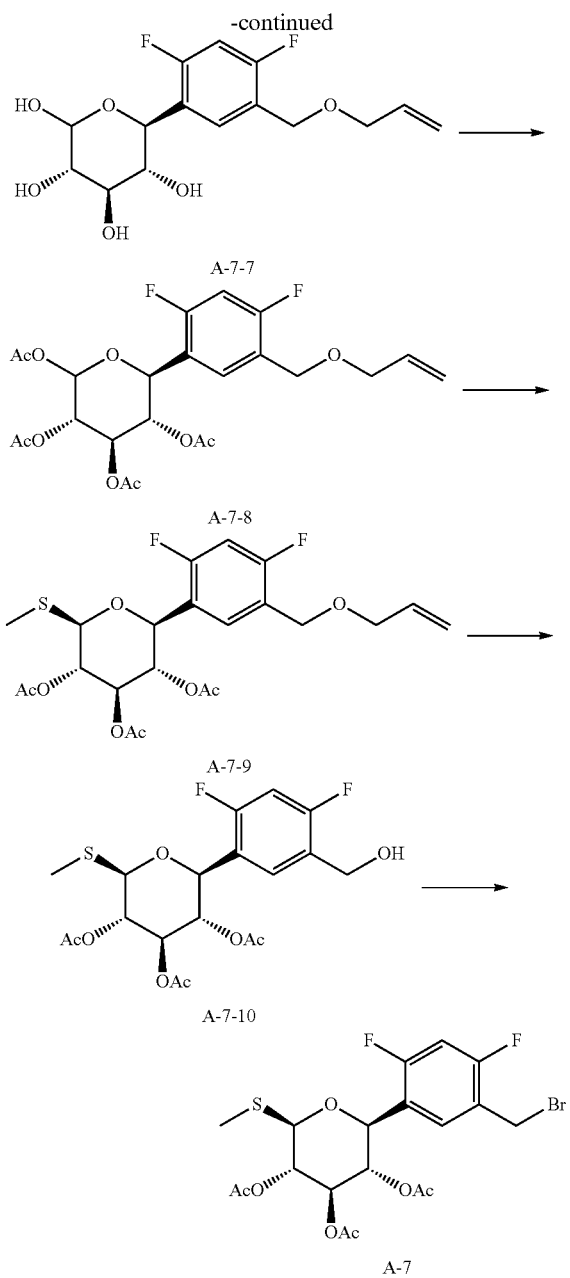

Step 2: Synthesis of Compound a-7-3

Sodium hydroxide (20.86 g, 521.45 mmol, 5 eq) was added to water (60 mL) at 0° C. and the mixture was stirred until sodium hydroxide was dissolved completed. To the solution was added toluene (180 mL), followed by compound A-7-2 (24.4 g, 104.29 mmol, 1 eq) and tetrabutylammonium bromide (TBAB) (3.36 g, 10.43 mmol, 0.1 eq). The reaction was stirred at 25° C. for 0.5 hours, and then Allyl bromide (18.92 g, 156.43 mmol, 13.52 mL, 1.5 eq) was added to the mixture. The reaction was warmed up to 50° C. and stirred for 10.5 hours. The mixture was stratified after standing. The organic phase was separated and the aqueous phase was extracted with ethyl acetate (80 mL*2). The organic phases were combined and washed with saturated brine (80 mL*2), dried over anhydrous sodium sulfate, and concentrated under reduced pressure to obtain a yellow oil. The yellow oil was added with toluene (50 mL) and the mixture was concentrated under reduced pressure again to obtain compound A-7-3, which was directly used in the next step without purification.

Step 3: Synthesis of Compound A-7-5

To a solution of compound A-1-4 (10.91 g, 39.91 mmol, 1 eq) in anhydrous tetrahydrofuran (200 mL) was added dropwise with a solution of tert-Butylmagnesium chloride (1.7 M, 37.56 mL, 1.6 eq) under nitrogen protection at 0° C. After the dropwise addition was completed, the reaction was stirred at 0 to 5° C. for 0.5 hours. Compound A-7-3 (10.5 g, 39.91 mmol, 1 eq) was added to the reaction under nitrogen protection. The mixture was cooled to −70° C., and a solution of n-butyllithium (2.5 M, 20.75 mL, 1.3 eq) was added dropwise to the reaction. After the dropwise addition was completed, the reaction was stirred at −70° C. for 0.5 hours, then the mixture was warmed up to 25° C. and reacted for 2 hours. After the reaction was completed, a saturated aqueous solution of ammonium chloride solution (50 mL) was added dropwise at 0 to 10° C. to quench the reaction, the mixture was extracted with ethyl acetate (80 mL*2). The organic phases were combined, dried over anhydrous sodium sulfate and concentrated under reduced pressure to obtain a crude product. The crude product was separated by column chromatography (petroleum ether:ethyl acetate=10:1 to 2:1) to obtain compound A-7-5, which was confirmed by LCMS, LC-MS (m/z) 393.2 [M+Na]+.

Step 4: Synthesis of Compound A-7-6

Sodium borohydride (469.29 mg, 12.41 mmol, 0.8 eq) was dissolved in sodium hydroxide aqueous solution (1 M, 4.65 mL, 0.3 eq) and then added to a mixture of Compound A-7-5 (6.5 g, 15.51 mmol, 1 eq) and cerium trichloride (4.59 g, 18.61 mmol, 1.17 mL, 1.2 eq) in methanol (80 mL). The reaction was stirred at 25° C. for 0.5 hours. After the reaction was completed, the reaction was quenched by saturated ammonium chloride aqueous solution (30 mL), the mixture was concentrated under reduce pressure and the residue was added with ethyl acetate (150 mL) and anhydrous magnesium sulfate (20 g). The mixture was filtered through celite, and the filter cake was washed with ethyl acetate (30 mL*3). The combined filtrates were concentrated under reduced pressure to obtain compound A-7-6, which was confirmed by LCMS, LC-MS (m/z) 390.2 [M+H$_2$O]+.

Step 5: Synthesis of Compound A-7-7

A mixture of compound A-7-6 (8 g, 21.48 mmol, 1 eq) in acetic acid (80 mL) and water (80 mL) was warmed up to

Step 1: Synthesis of Compound A-7-2

Sodium borohydride (7.28 g, 192.43 mmol, 3.04 eq) was added in batches to a solution of A-7-1 (14 g, 63.35 mmol, 1 eq) in methanol (60 mL) at 0° C. under nitrogen protection. The reaction was stirred for 2 hours at 0° C. After the reaction was completed, an aqueous solution of saturated ammonium chloride (20 mL) was added dropwise at 0° C. and continuously stirred for 30 min to quench the reaction. The mixture was concentrated under reduced pressure to get the residue. Ethyl acetate (300 mL) and an aqueous solution of saturated sodium chloride (100 mL) were added to the residue and stirred. The organic phase was separated and dried over anhydrous sodium sulfate and concentrated under reduced pressure to get the crude product. The crude product was purified by column chromatography (petroleum ether: ethyl acetate=1:0 to 10:1) to obtain compound A-7-2.

100° C. and stirred for 16 hours. After the reaction was completed, the reaction was concentrated under reduced pressure to get the residue. The residue was concentrated under reduce pressure twice with toluene (50 mL) to obtain compound A-7-7, which was confirmed by LCMS, LC-MS (m/z) 350.1 [M+H$_2$O]$^+$.

Step 6: Synthesis of Compound A-7-8

A mixture of compound A-7-7 (8 g, 24.07 mmol, 1 eq), triethylamine (19.49 g, 192.60 mmol, 26.81 mL, 8 eq), and 4-dimethylaminopyridine (294.12 mg, 2.41 mmol, 0.1 eq) in acetonitrile (100 mL) were added with acetic anhydride (14.75 g, 144.45 mmol, 13.53 mL, 6 eq). The mixture was stirred at 25° C. for 16 hours. After the reaction was completed, the mixture was concentrated under reduced pressure, and the residue was diluted with ethyl acetate (100 mL), washed with saturated KHSO$_4$ solution (80 mL*5), then dried over anhydrous sodium sulfate and concentrated under reduced pressure. The residue was purified by column chromatography (petroleum ether:ethyl acetate=8:1 to 2:1) to obtain a yellow oil. The yellow oil was dissolved with ethyl acetate (100 mL), and washed with aqueous solution of hydrochloric acid (1 N, 80 mL*4) and saturated brine (80 mL) sequentially. The organic phase was dried over anhydrous sodium sulfate and concentrated, and the residue was concentrated under reduced pressure with toluene (50 mL) twice to obtain compound A-7-8, which was confirmed by LCMS, LC-MS (m/z) 523.1 [M+Na]$^+$.

Step 7: Synthesis of Compound A-7-9

Trimethylsilyl trifluoromethanesulfonate (12.44 g, 55.95 mmol, 10.11 mL, 4 eq.) was added to a mixture of compound A-7-8 (7 g, 13.99 mmol, 1 eq.) and thiourea (3.73 g, 48.96 mmol, 3.5 eq.) in anhydrous dioxane (100 mL) under nitrogen protection. The reaction was stirred at 80° C. for 0.5 hours. The reaction was cooled to 10° C., and added with iodomethane (5.96 g, 41.96 mmol, 2.61 mL, 3 eq.) and diisopropylethylamine (9.04 g, 69.94 mmol, 12.18 mL, 5 eq.) sequentially, then the mixture was warmed up to 25° C. and stirred for 10 hours. The reaction was quenched by water (80 mL) and the mixture was extracted with ethyl acetate (100 mL*3). The organic phases were combined, washed with saturated brine (150 mL), and concentrated under reduced pressure to obtain a crude product. The crude product was purified by column chromatography (petroleum ether:ethyl acetate=10:1 to 3:1) to obtain compound A-7-9, which was confirmed by $^1$H NMR and LCMS, $^1$H NMR (400 MHz, CDCl$_3$) δ 1.86 (s, 3H), 2.04 (s, 3H), 2.12 (s, 3H), 2.21 (s, 3H), 4.00-4.09 (m, 2H), 4.50-4.61 (m, 3H), 4.76-4.83 (m, 1H), 5.18-5.46 (m, 5H), 5.89-6.03 (m, 1H), 6.80 (t, J=9.79 Hz, 1H), 7.49-7.57 (m, 1H), LC-MS (m/z) 534.4 [M+2Na]$^+$.

Step 8: Synthesis of Compound A-7-10

A mixed of compound A-7-9 (2.5 g, 5.12 mmol, 1 eq), barbituric acid (1.31 g, 10.24 mmol, 2 eq) and Pd(PPh$_3$)$_4$ (887.08 mg, 767.66 µmol, 0.15 eq) in ethanol (60 mL) was stirred at 50° C. for 20 hours under nitrogen protection. The reaction solution was cooled and concentrated under reduced pressure. The residue was purified by column chromatography (petroleum ether:ethyl acetate=6:1 to 2:1) to obtain compound A-7-10, which was confirmed by LCMS, LC-MS (m/z) 471.2 [M+Na]$^+$.

Step 9: Synthesis of Compound A-7

Phosphorus tribromide (271.64 mg, 1.00 mmol, 94.32 µL, 1.5 eq) was added to a solution of compound A-7-10 (300 mg, 668.99 µmol, 1 eq) in anhydrous tetrahydrofuran (5 mL) at 0° C. The reaction was stirred at 20° C. for 3 hours. After the reaction was completed, the reaction was quenched by 1 N potassium carbonate aqueous solution (20 mL) at 0° C., and the mixture was extracted with ethyl acetate (20 mL*2). The organic phases were combined, dried over anhydrous sodium sulfate and concentrated under reduced pressure to obtain a crude product. The crude product was purified by column chromatography (petroleum ether:ethyl acetate=10:1 to 3:1) to obtain compound A-7. $^1$H NMR (400 MHz, CDCl$_3$) δ ppm 1.78 (s, 3H), 1.95 (s, 3H), 2.03 (s, 3H), 2.14 (s, 3H), 4.32-4.44 (m, 2H), 4.49 (d, J=10.01 Hz, 1H), 4.68 (d, J=10.01 Hz, 1H), 5.14 (t, J=9.69 Hz, 2H), 5.26-5.33 (m, 1H), 6.74 (t, J=9.69 Hz, 1H), 7.40 (t, J=7.88 Hz, 1H).

Fragment A-8 in Table 2 was synthesized by referring to the synthesis methods of steps 1 to 9 in reference embodiment 7.

TABLE 2

| Reference embodiment | Fragment | Structure | NMR |
|---|---|---|---|
| 8 | A-8 | (structure shown) | $^1$H NMR (400 MHz, CDCl$_3$) δ ppm 1.80 (s, 3 H), 2.01 (s, 3H), 2.09 (s, 3 H), 2.18 (s, 3 H), 2.39 (s, 3 H), 4.44-4.47 (m, 2H), 4.54 (d, J = 10.04 Hz, 1H), 4.65 (d, J = 10.04 Hz, 1 H), 5.24 (dt, J = 19.83, 9.66 Hz, 2 H), 5.32-5.39 (m, 1 H), 6.85 (d, J = 10.29 Hz, 1 H), 7.35 (d, J = 7.78 Hz, 1 H) |

Reference Embodiment 9: Fragment B-1

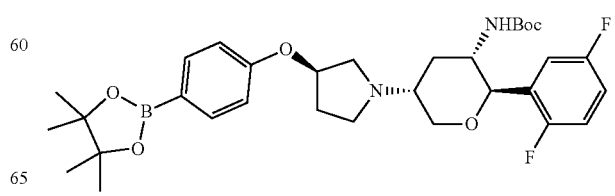

Synthetic Route

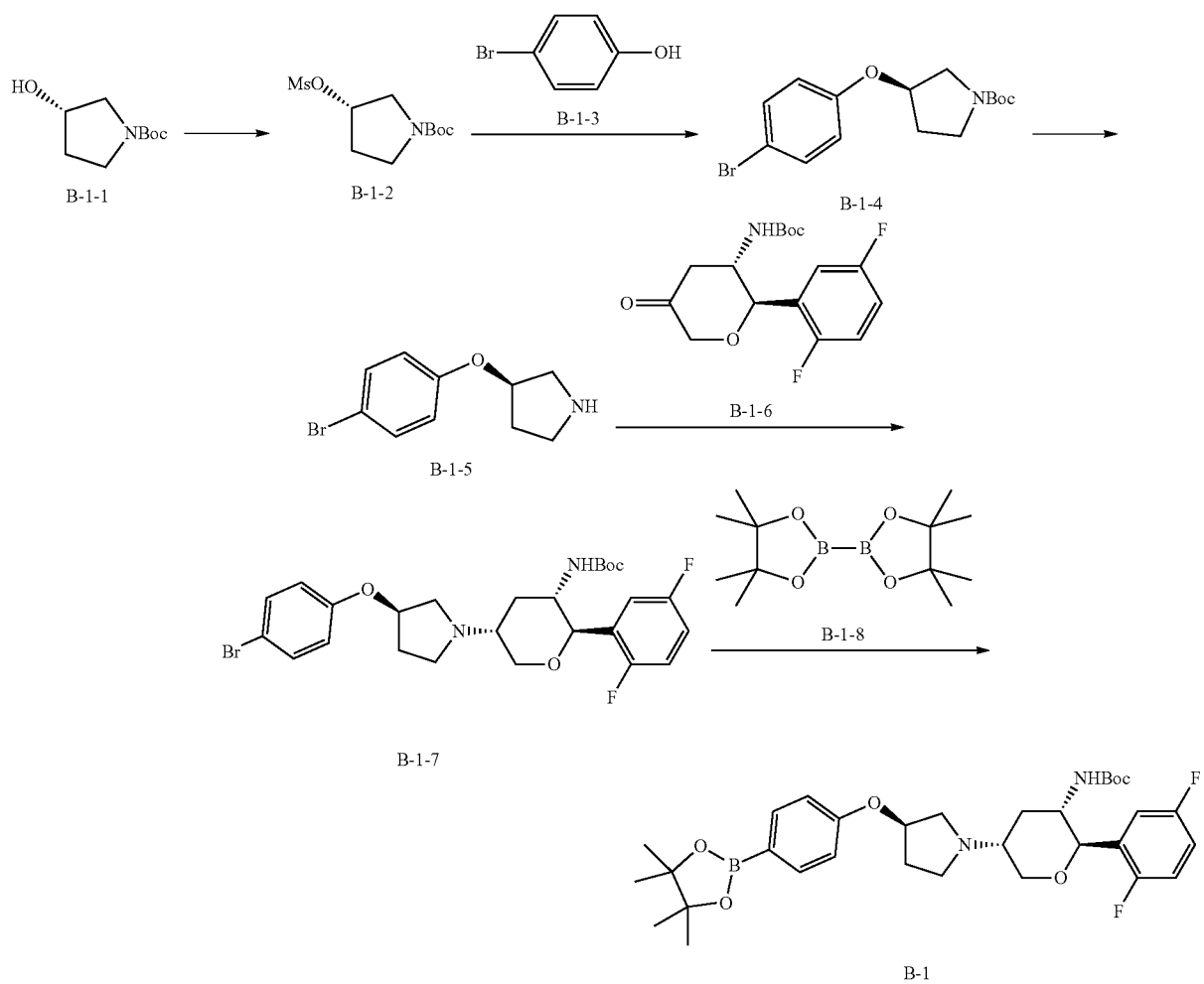

Step 1: Synthesis of Compound B-1-2

Triethylamine (27.02 g, 267.04 mmol, 37.17 mL, 2 eq) was added to a solution of compound B-1-1 (25 g, 133.52 mmol, 1 eq) in dichloromethane (110 mL). The mixture was cooled to 0° C., and methanesulfonyl chloride (15.30 g, 133.52 mmol, 10.33 mL, 1 eq) was added dropwise to the reaction. After the addition was completed, the reaction was warmed from 0° C. to 15° C. and stirred for 3 hours. After the reaction was completed, the reaction was cooled to 0° C. and added slowly with water (100 mL) at 0° C. to quench the reaction. The mixture was extracted with dichloromethane (100 mL*2), and the combined organic phases were washed with saturated brine (100 mL), dried over anhydrous sodium sulfate and concentrated under reduced pressure to obtain compound B-1-2, which was directly used in the next reaction step.

Step 2: Synthesis of Compound B-1-4

To a mixture of Compound B-1-2 (6.00 g, 22.61 mmol, 1.00 eq) in N,N-dimethylformamide (10.00 mL), was added with cesium carbonate (14.73 g, 45.22 mmol, 2.00 eq) and compound B-1-3 (3.91 g, 22.61 mmol, 1.00 eq). The mixture was stirred at 80° C. for 3 hours. After the reaction was completed, the reaction was quenched by water (50 mL) and extracted with ethyl acetate (30 mL*3). The organic phases were combined, washed with water (30 mL*3) and saturated brine (30 mL) sequentially, dried over anhydrous sodium sulfate and concentrated under reduced pressure to obtain a crude product. The crude product was purified by column chromatography (petroleum ether:ethyl acetate=1:0 to 2:1) to obtain compound B-1-4. $^1$H NMR (400 MHz, CD$_3$OD) δ 7.41-7.34 (m, 2H), 6.78-6.74 (m, 2H), 4.15-4.12 (m, 1H), 3.64-3.52 (m, 4H), 2.18-2.07 (m, 2H), 1.157 (s, 9H).

Step 3: Synthesis of Compound B-1-5

Compound B-1-4 (3.00 g, 8.77 mmol, 1.00 eq) was added to a solution of hydrogen chloride in ethyl acetate (10 mL, 4 M), and the reaction was carried out at 20° C. for 1 hour. After the reaction was completed, water (30 mL) was added to quench the reaction, and the mixture was washed with ethyl acetate (20 mL). The aqueous phase was adjusted to pH=7 with saturated sodium bicarbonate aqueous solution and extracted with ethyl acetate (30 mL). The organic phase was washed with saturated brine (20 mL), dried over anhydrous sodium sulfate and concentrated under reduced pressure to obtain a crude product of compound B-1-5. The crude product was used directly in the next reaction step without further purification. $^1$H NMR (400 MHz, MeOD-d$_4$) δ 7.39-7.35 (m, 2H), 6.76-6.74 (m, 2H), 5.30 (m, 1H), 3.31-3.13 (m, 4H), 2.15-2.05 (m, 2H).

Step 4: Synthesis of Compound B-1-7

Compound B-1-6 (24.67 g, 75.38 mmol, 1.05 eq) was dissolved in a solution of anhydrous dichloromethane (200 mL) and anhydrous N,N-dimethylformamide (200 mL) under nitrogen protection, then compound B-1-5 (20 g, 71.79 mmol, 1 eq, HCl) was added at 20° C. and reacted for 1 hour. The reaction was cooled to −70° C. and then continuously stirred for 0.5 hours. Sodium borohydride acetate (30.43 g, 143.60 mmol, 2 eq) was added slowly to the reaction in 30 min, controlling the temperature below −60° C. during the addition. The reaction was stirred at −70° C. for 17.5 hours. After the reaction was completed, the mixture was concentrated under reduced pressure, and the residue was diluted with water (600 mL) slowly to precipitate a large amount of white flocculent solid, the mixture was stirred for 1 hour and filtered, the filter cake was washed with water (100 mL*3). The filter cake was added with ethanol (500 mL) and stirred for 12 hours. After filtration, the filter cake was collected and washed with ethanol (100 mL), dried under reduced pressure to obtain compound B-1-7. $^1$H NMR (CDCl$_3$-d) δ 7.74 (d, J=8.5 Hz, 2H), 7.21 (br s, 1H), 7.02-6.90 (m, 2H), 6.85-6.82 (m, 1H), 6.89-6.82 (m, 2H), 4.88 (br dd, J=7.2, 3.1 Hz, 1H), 4.47 (br d, J=9.5 Hz, 1H), 4.27 (br d, J=10.0 Hz, 1H), 4.23-4.18 (m, 1H), 3.81-3.68 (m, 1H), 3.38 (br t, J=10.7 Hz, 1H), 3.02-2.89 (m, 3H), 2.64-2.51 (m, 2H), 2.45 (br d, J=11.0 Hz, 1H), 2.39-2.26 (m, 1H), 2.07-1.95 (m, 1H), 1.51 (q, J=11.8 Hz, 1H), 1.33 (s, 12H), 1.26 (br s, 9H).

Step 5: Synthesis of Compound B-1

Bis(pinacolato)diboron (4.88 g, 19.20 mmol, 1.25 eq), potassium acetate (4.52 g, 46.08 mmol, 3 eq) and Pd(dppf)Cl$_2$·DCM (3.76 g, 4.61 mmol, 0.3 eq) were added sequentially to a solution of compound B-1-7 (8.5 g, 15.36 mmol, 1 eq) in anhydrous dioxane (170 mL) under nitrogen protection. The reaction was warmed to 100° C. and stirred for 7 hours. The mixture was concentrated under reduced pressure and diluted with dichloromethane (500 mL). The organic phase was washed with water (200 mL×3), dried over anhydrous sodium sulfate and filtered. The filtrate was concentrated under reduced pressure to obtain a crude product. The crude product was purified by column chromatography (petroleum ether:ethyl acetate=5:1 to 0:1) to obtain compound B-1. $^1$H NMR (CDCl$_3$) δ 7.74 (d, J=8.8 Hz, 2H), 7.25-7.15 (m, 1H), 7.00-6.87 (m, 2H), 6.84 (d, J=8.8 Hz, 2H), 4.92-4.82 (m, 1H), 4.48 (br d, J=8 Hz, 1H), 4.27 (br d, J=9.8 Hz, 1H), 4.24-4.18 (m, 1H), 3.78-3.66 (m, 1H), 3.38 (br t, J=10.8 Hz, 1H), 3.07-2.84 (m, 3H), 2.65-2.50 (m, 2H), 2.49-2.39 (m, 1H), 2.37-2.27 (br d, J=7.5 Hz, 1H), 2.04-1.98 (m, 1H), 1.69 (s, 3H), 1.52 (q, J=12 Hz, 1H), 1.33 (s, 12H), 1.26 (s, 9H).

Embodiment 1: WX001

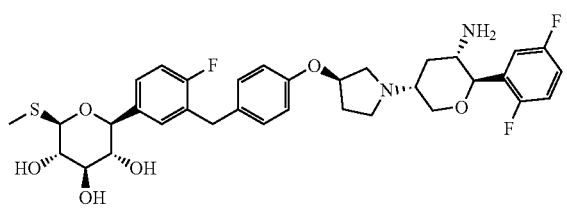 [SMILES: CS[C@H]1O[C@@H](c2ccc(F)c(Cc3ccc(O[C@@H]4CCN([C@H]5CO[C@H](c6cc(F)ccc6F)[C@@H](N)C5)C4)cc3)c2)[C@H](O)[C@@H](O)[C@@H]1O]

Synthetic Route

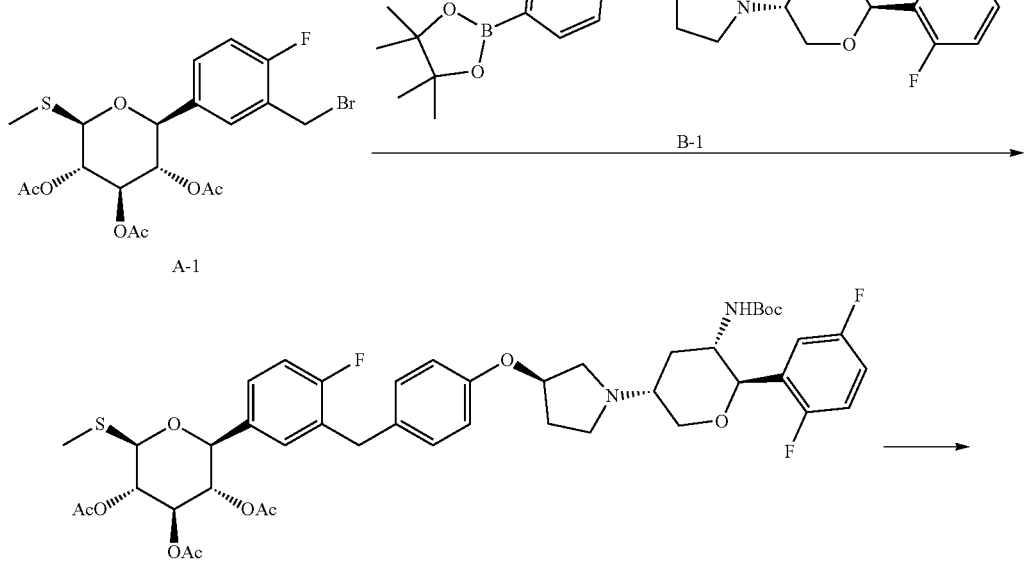

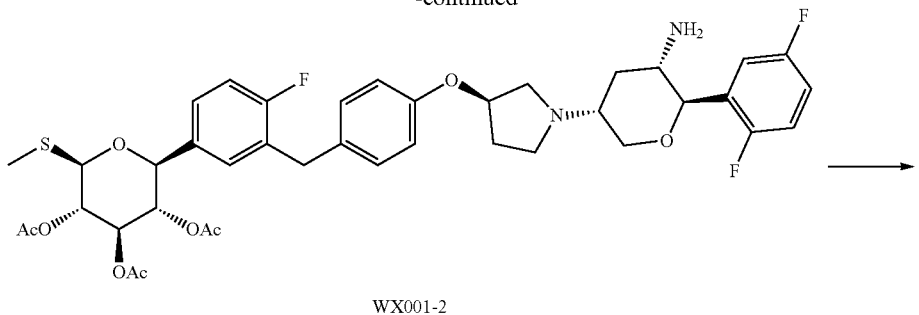

WX001-2

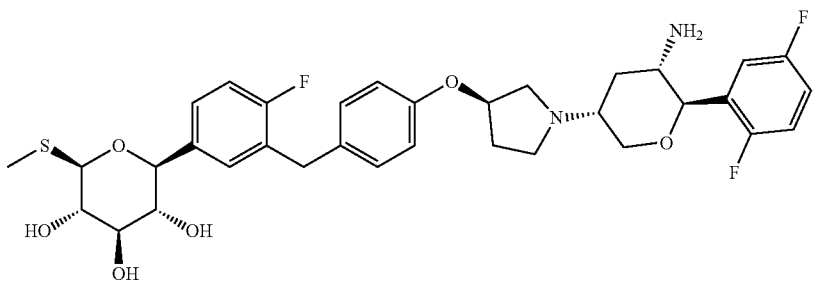

WX001

Step 1: Synthesis of Compound WX001-1

A mixture of B-1 (126.59 mg, 210.81 μmol), A-1 (0.104 g, 210.81 μmol), sodium carbonate (44.69 mg, 421.62 μmol) and tetrakis(triphenylphosphine)palladium (48.72 mg, 42.16 μmol) in a solution of toluene (2.4 mL), ethanol (0.6 mL) and water (0.6 mL) was stirred at 50° C. for 16 hours under nitrogen protection. After the reaction was completed, the mixture was concentrated under reduced pressure and the residue was diluted with dichloromethane (30 mL) and washed with water (20 mL*2). The organic phase was dried over anhydrous sodium sulfate and concentrated under reduced pressure to obtain crude product. The crude product was stirred with ethanol (9.50 mL) for 3 hours and then the mixture was filtered. The solid was washed with ethanol (2 mL*3) and dried under reduced pressure to obtain compound WX001-1. MS m/z: 887.5 [M+1]+.

Step 2: Synthesis of Compound WX001-2

A solution of hydrogen chloride in ethyl acetate (4 M, 2.5 mL) was added to a solution of compound WX001-1 (0.128 g, 144.31 μmol) in ethyl acetate (2.5 mL). The reaction was stirred at 20° C. for 16 hours. After the reaction was completed, a crude product of compound WX001-2 was obtained by concentration under reduced pressure. The crude product was used directly in the next reaction step without further purification.

Step 3: Synthesis of Compound WX001

Potassium carbonate (108.28 mg, 783.42 μmol) was added to a solution of the crude product of compound WX001-2 (0.129 g, 156.68 μmol) in methanol (5 mL). The reaction was stirred at 25° C. for 2 hours. The mixture was filtered after the reaction was completed, and the filtrate was concentrated under reduced pressure and the residue was diluted with dichloromethane (20 mL). The organic phase was washed with water (15 mL*3). The aqueous phases were combined and extracted with dichloromethane (10 mL*2). All organic phases were combined, dried over anhydrous sodium sulfate and concentrated under reduced pressure to obtain a crude product. The crude product was purified by preparative high performance liquid chromatography (acetonitrile/water/ammonium carbonate/ammonia system) to obtain the compound WX001. $^1$H NMR (400 MHz, CDCl$_3$) δ 7.25-7.17 (m, 1H), 7.17-7.06 (m, 4H), 7.06-6.92 (m, 3H), 6.77 (brd, J=7.6 Hz, 2H), 4.79 (brs, 1H), 4.34 (brd, J=8.8 Hz, 1H), 4.24-4.02 (m, 3H), 4.01-3.77 (m, 2H), 3.66-3.52 (m, 1H), 3.52-3.29 (m, 3H), 3.14-3.01 (m, 1H), 2.91-2.82 (m, 1H), 2.79-2.70 (m, 2H), 2.62-2.55 (m, 2H), 2.44-2.30 (m, 2H), 2.27-2.21 (m, 1H), 2.16 (br s, 3H), 2.07-1.89 (m, 1H), 1.49-1.37 (m, 1H).

Embodiment 2: WX002

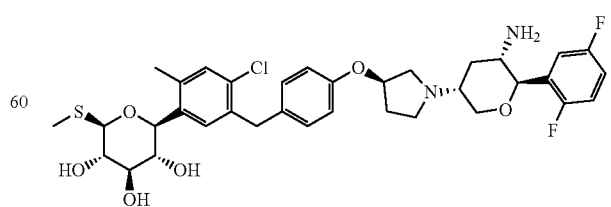

Synthetic Route

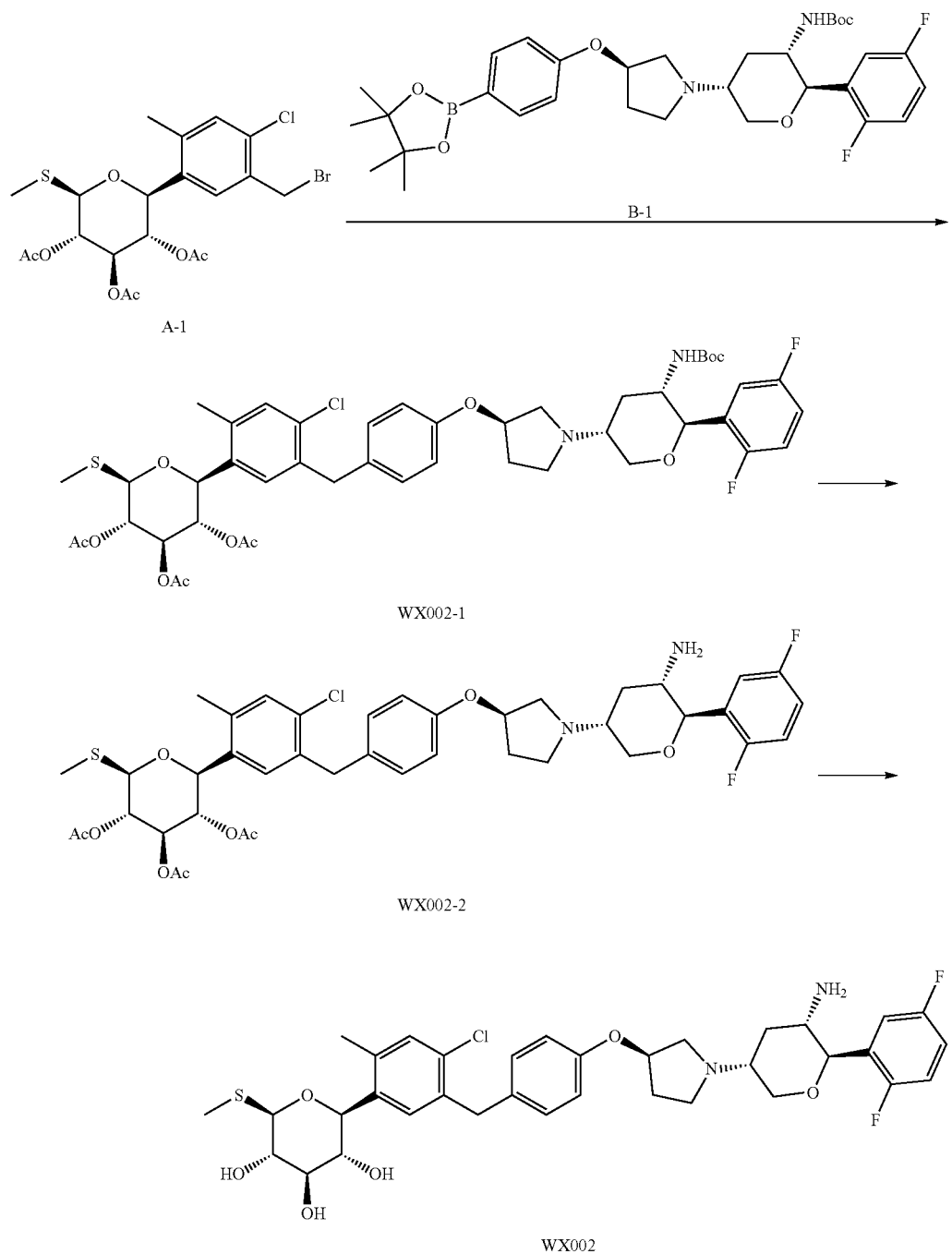

Step 1: Synthesis of WX002-1

Compound A-2, compound B-1 (309.52 mg, 515.44 μmol, 1 eq), tetrakis(triphenylphosphine)palladium (59.56 mg, 51.54 μmol, 0.1 eq) and potassium carbonate (142.47 mg, 1.03 mmol, 2 eq) were suspended in a mixture of dioxane (4 mL) and water (1 mL) under nitrogen protection, the reaction was stirred at 50° C. for 5 hours. The crude product from reaction was purified by column chromatography (dichloromethane:methanol=1:0 to 4:1) to obtain WX002-1, LC-MS of the product (m/z) 917.8 [M+H]$^+$.

Step 2: Synthesis of WX002-2

WX002-1 (190 mg, 207.10 μmol, 1 eq) was dissolved in dichloromethane (2.5 mL), and trifluoroacetic acid (770.00 mg, 6.75 mmol, 0.5 mL, 32.61 eq) was added dropwise to the reaction. The reaction was stirred at 25° C. for 2 hours. After the reaction was completed, the mixture was concentrated under reduced pressure, the residue was added with saturated sodium bicarbonate (10 mL) and dichloromethane (10 mL), then the mixture was stirred and the organic phase was separated and concentrated under reduced pressure to obtain WX002-2, LC-MS of the product (m/z) 817.2 [M+H]+.

Step 3: Synthesis of WX002

Potassium carbonate (135.28 mg, 978.79 μmol, 5 eq) was added to a solution of WX002-2 (160 mg, 195.76 μmol, 1 eq) in methanol (2 mL) at 25° C., then the mixture was stirred for 2 hours. After the reaction was completed, the reaction was filtered, and the filtrate was concentrated under reduced pressure to obtain a crude product.

The crude product was purified by preparative chromatography to obtain WX002, which was confirmed by LCMS, LC-MS (m/z) 691.1 [M+H]+, 1H NMR (400 MHz, CD3OD) δ ppm 1.64 (q, J=11.54 Hz, 1H), 1.95-2.04 (m, 1H), 2.14 (s, 3H), 2.28-2.36 (m, 1H), 2.38 (s, 3H), 2.50 (br d, J=14.31 Hz, 1H), 2.62-2.75 (m, 2H), 2.91-3.09 (m, 3H), 3.21-3.30 (m, 1H), 3.35-3.53 (m, 4H), 3.94-4.07 (m, 2H), 4.21-4.31 (m, 1H), 4.42 (d, J=9.54 Hz, 1H), 4.47 (d, J=9.03 Hz, 2H), 4.59 (br s, 1H), 6.82 (d, J=8.78 Hz, 2H), 7.07-7.38 (m, 6H), 8.47 (s, 1H).

Referring to the synthesis method of steps 1 to 3 in embodiment 2, fragments A-3, A-4, and A-6 were used instead of A-2 to synthesize embodiments 3-5 in Table 3.

TABLE 3

| Embodiment | Fragment A | Fragment B |
|---|---|---|
| 3 | 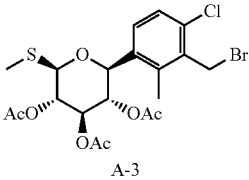 [SMILES: CS[C@H]1O[C@@H](c2ccc(Cl)c(CBr)c2C)[C@H](OC(C)=O)[C@@H](OC(C)=O)[C@@H]1OC(C)=O ; "A-3"]<br>A-3 | 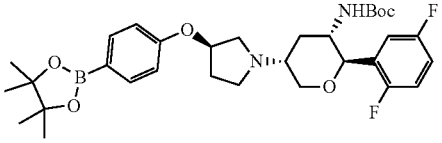<br>B-1 |
| 4 | 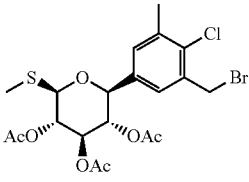<br>A-4 | |
| 5 | 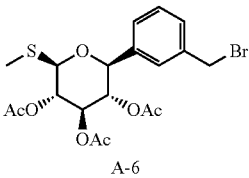 [SMILES: CS[C@H]1O[C@@H](c2cccc(CBr)c2)[C@H](OC(C)=O)[C@@H](OC(C)=O)[C@@H]1OC(C)=O ; "A-6"]<br>A-6 | |

| Embodiment | Compound | Structure |
|---|---|---|
| 3 | WX003 | 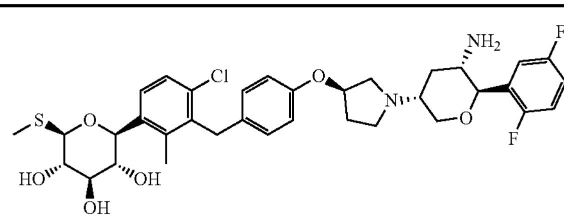 |
| 4 | WX004 | 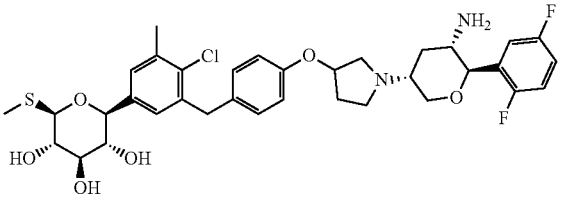 [SMILES: CS[C@H]1O[C@@H](c2cc(C)c(Cl)c(Cc3ccc(OC4CCN([C@H]5CO[C@H](c6cc(F)ccc6F)[C@@H](N)C5)C4)cc3)c2)[C@H](O)[C@@H](O)[C@@H]1O] |

TABLE 3-continued
| 5 | WX005 | 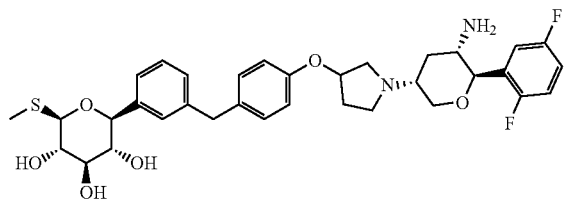 [SMILES: CS[C@H]1O[C@@H](c2cccc(Cc3ccc(OC4CCN([C@H]5CO[C@H](c6cc(F)ccc6F)[C@@H](N)C5)C4)cc3)c2)[C@H](O)[C@@H](O)[C@@H]1O] |
Embodiment 6: WX006
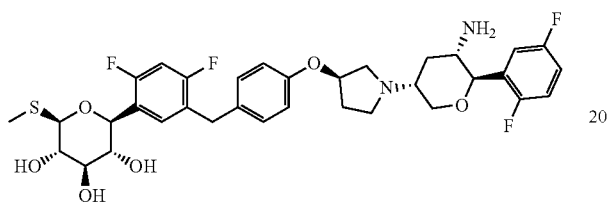
Synthetic Route
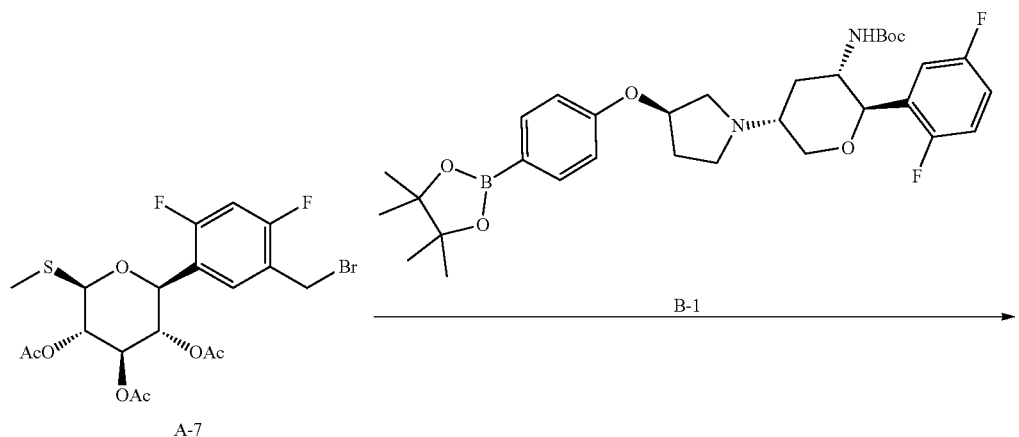
A-7
B-1
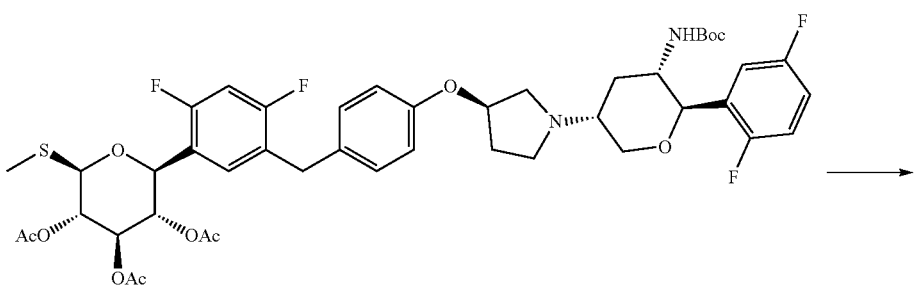
WX006-1

-continued

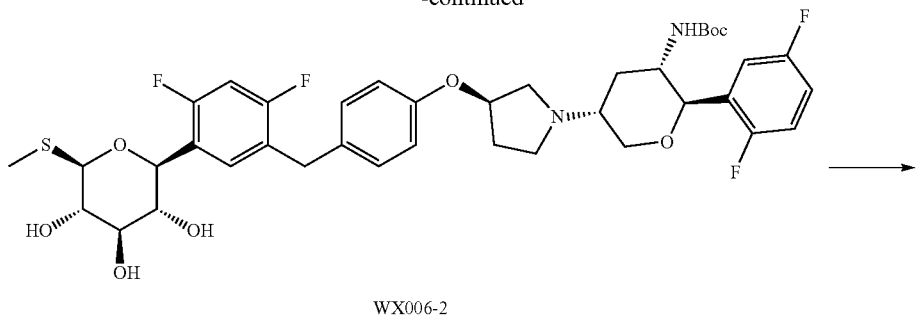
WX006-2

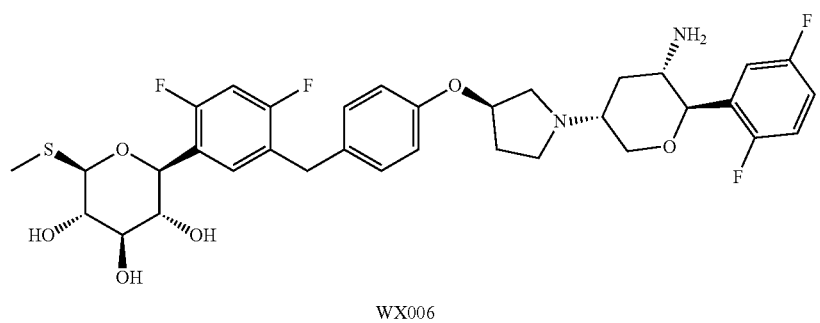
WX006

Step 1: Synthesis of WX006-1

A mixture of compound A-7 (170 mg, 332.47 μmol, 1 eq), compound B-1 (199.65 mg, 332.47 μmol, 1 eq), tetrakis(triphenylphosphine)palladium (38.42 mg, 33.25 μmol, 0.1 eq) and sodium carbonate (105.71 mg, 997.40 μmol, 3 eq) in a mixture of dioxane (4 mL) and water (1 mL) was stirred at 50° C. for 7 hours under nitrogen protection. After the reaction was completed, the mixture was concentrated under reduced pressure to obtain a crude product of WX006-1, which was confirmed by LCMS, LC-MS (m/z) 906.5 [M+H]$^+$.

Step 2: Synthesis of WX006-2

Sodium methanol (23.88 mg, 442.01 μmol, 2 eq) was added to a mixture of the crude product of WX006-1 (200 mg, 221.00 μmol, 1 eq) and methanol (5 mL). The reaction was stirred at 25° C. for 2 hours. After the reaction was completed, the mixture was concentrated under reduced pressure, and the residue was purified twice by silica gel preparative plates (the ratio of developing solvent was dichloromethane:methanol=15:1 and dichloromethane:methanol=10:1 sequentially) to obtain WX006-2, which was confirmed by LCMS, LC-MS (m/z) 779.3 [M+H]$^+$.

Step 3: Synthesis of WX006

Trifluoroacetic acid (770.00 mg, 6.75 mmol, 0.5 mL, 58.44 eq) was added to a solution of WX006-2 (90 mg, 115.56 μmol, 1 eq) in dichloromethane (3 mL). The reaction was stirred at 20° C. for 0.5 hours. After the reaction was completed, the mixture was concentrated under reduced pressure. The residue was dissolved in dichloromethane (20 mL) and washed with 1 N potassium carbonate aqueous solution (15 mL). The organic phase was concentrated under reduced pressure to obtain crude product. The crude product was purified by silica gel preparative plate (dichloromethane:methanol=8:1, Rf=0.2), followed by supercritical chiral preparation (column type: DAICEL CHIRALPAK AS (250 mm*30 mm, 10 μm), mobile phase A was supercritical carbon dioxide, phase B: 0.1% ammonia-ethanol solution; ratio B %: 35%-35%) to obtain WX006, which was confirmed by LCMS, LC-MS (m/z) 679.4 [M+H]$^+$, $^1$H NMR (400 MHz, CD$_3$OD) δ ppm 1.45-1.56 (m, 1H), 1.93-2.01 (m, 1H), 2.14 (s, 3H), 2.28-2.38 (m, 1H), 2.39-2.47 (m, 1H), 2.57-2.66 (m, 2H), 2.89-2.97 (m, 2H), 2.97-3.05 (m, 2H), 3.34-3.42 (m, 3H), 3.45-3.52 (m, 2H), 3.93 (s, 2H), 4.18-4.24 (m, 1H), 4.30 (d, J=9.54 Hz, 1H), 4.41 (d, J=9.54 Hz, 1H), 4.46-4.53 (m, 1H), 6.83 (d, J=8.53 Hz, 2H), 6.92 (t, J=10.04 Hz, 1H), 7.06-7.18 (m, 4H), 7.18-7.24 (m, 1H), 7.33 (t, J=8.03 Hz, 1H).

Referring to the synthesis method of steps 1 to 3 in embodiment 6, fragment A-5 was used instead of A-7 to synthesize embodiment 7 in Table 4.

TABLE 4
| Embodiment | Fragment A | Fragment B |
|---|---|---|
| 7 | 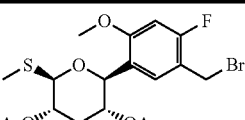<br>A-5 | 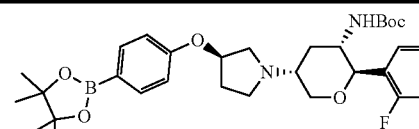<br>B-1 |
| Embodiment | Compound | Structure |
|---|---|---|
| 7 | WX007 | 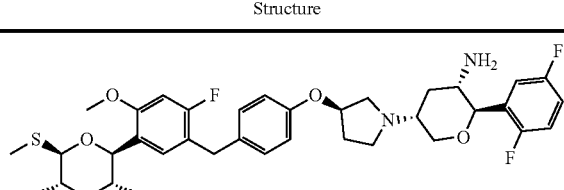 |
Embodiment 8: WX008
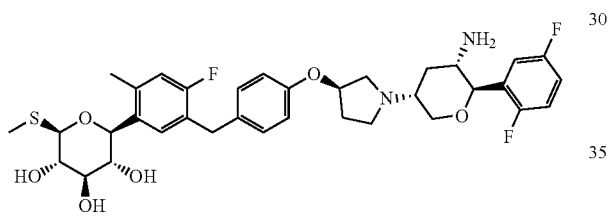
Synthetic Route
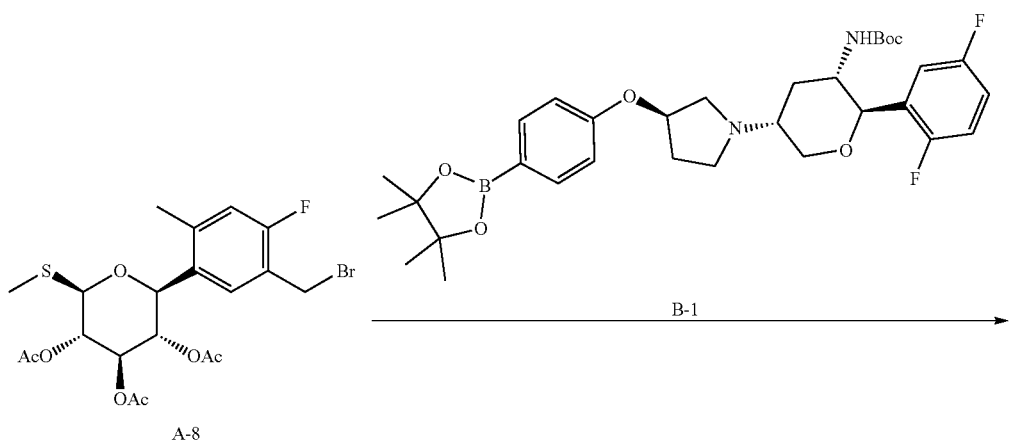

-continued

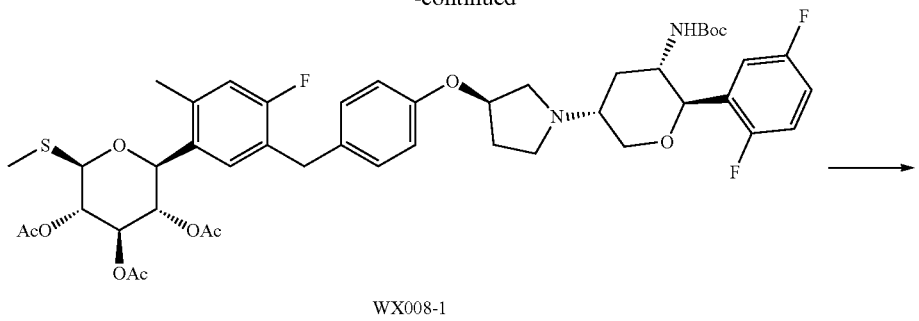

WX008-1

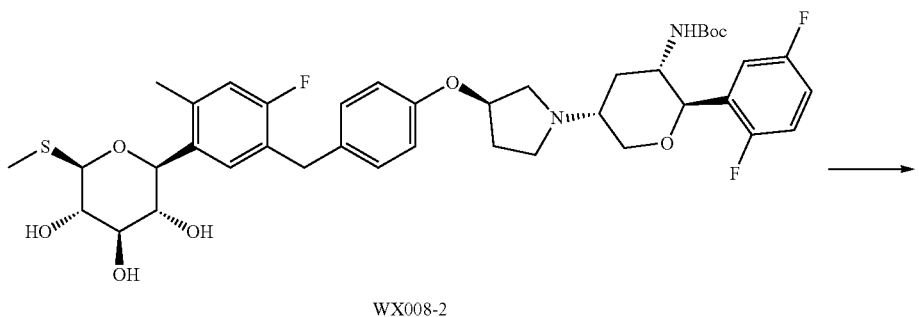

WX008-2

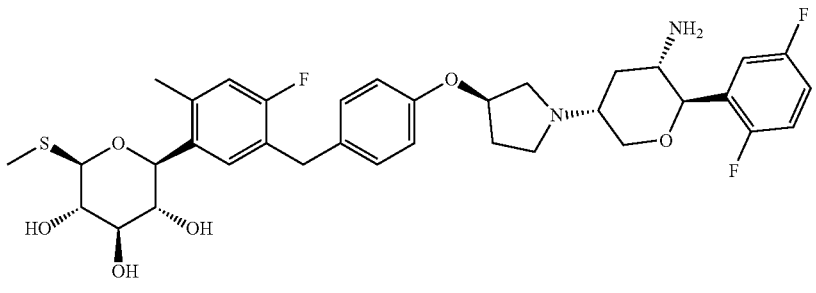 [SMILES: CS[C@H]1O[C@@H](c2cc(Cc3ccc(O[C@@H]4CCN([C@H]5CO[C@H](c6cc(F)ccc6F)[C@@H](N)C5)C4)cc3)c(F)cc2C)[C@H](O)[C@@H](O)[C@@H]1O]

WX008

Step 1: Synthesis of WX008-1

A mixture of A-8 (227 mg, 447.41 μmol, 1 eq), B-1 (322.40 mg, 536.89 μmol, 1.2 eq), potassium carbonate (123.67 mg, 894.82 μmol, 2 eq) and tris(dibenzylideneacetone)dipalladium (40.97 mg, 44.74 μmol, 0.1 eq) in a mixture of water (1.5 mL) and dioxane (5 mL) was stirred at 50° C. for 7 hours under nitrogen protection. After the reaction was completed, the reaction solution was concentrated under reduced pressure to obtain a crude product of WX008-1, which was confirmed by LCMS, LC-MS (m/z) 901.3 [M+H]$^+$.

Step 2: Synthesis of WX008-2

Sodium methanol (53.36 mg, 987.80 μmol, 2 eq) was added to a mixture of WX008-1 (445 mg, 493.90 μmol, 1 eq) and methanol (3 mL), and the reaction was stirred at 25° C. for 2 hours. After the reaction was completed, the reaction solution was concentrated under reduced pressure to obtain a crude product. The crude product was purified by silica gel preparative plate (dichloromethane:methanol=10:1, Rf=0.12) to obtain WX008-2, which was confirmed by LCMS, LC-MS (m/z) 775.3 [M+H]$^+$.

Step 3: Synthesis of WX008

Trifluoroacetic acid (1.26 g, 11.02 mmol, 815.72 μL, 40.08 eq) was added to a solution of WX008-2 (213 mg, 274.88 μmol, 1 eq) in dichloromethane (3 mL), and the reaction was stirred at 25° C. for 1 hour. After the reaction was completed, the reaction solution was concentrated under reduced pressure to obtain a crude product. The crude product was purified by preparative high performance liquid chromatography (chromatographic column: Welch Xtimate C18 150*25 mm*5 μm; mobile phase: [H$_2$O(0.2% FA)-ACN]; B (ACN) %: 10%-40%, 6 min) to obtain WX008 formate, which was confirmed by LCMS, LC-MS (m/z) 675.3 [M+H]$^+$, $^1$H NMR (400 MHz, CD$_3$OD) δ ppm 1.29-1.34 (m, 1H), 1.59 (q, J=11.67 Hz, 1H), 1.97 (br dd, J=9.51, 6.63 Hz, 1H), 2.12 (s, 3H), 2.25-2.35 (m, 1H), 2.36 (s, 3H), 2.43-2.50 (m, 1H), 2.59-2.71 (m, 2H), 2.90-2.96 (m, 1H), 2.97-3.05 (m, 2H), 3.10-3.22 (m, 1H), 3.34-3.43 (m, 2H), 3.45-3.54 (m, 2H), 3.89 (s, 2H), 4.19-4.28 (m, 1H), 4.37-4.46 (m, 3H), 6.79 (d, J=8.75 Hz, 2H), 6.87 (d, J=11.01 Hz, 1H), 7.09-7.21 (m, 4H), 7.23-7.26 (m, 2H), 8.49 (s, 1H).

Proton nuclear magnetic resonance and mass spectrum data of each embodiment are shown in Table 5.

TABLE 5

Proton nuclear magnetic resonance and mass spectrum data of each embodiment

| Embodiment | Compound | $^1$H NMR | MS m/z |
|---|---|---|---|
| 1 | WX001 | $^1$H NMR(400 MHz, CDCl$_3$) δ 7.25-7.17 (m, 1 H), 7.17-7.069 (m, 4 H), 7.06-6.92 (m, 3H), 6.77 (br d, J = 7.6 Hz, 2H), 4.79 (br s, 1H), 4.34 (br d, J = 8.8 Hz, 1H), 4.24-4.02 (m, 3H), 4.01-3.77 (m, 2H), 3.66-3.52 (m, 1H), 3.52-3.29 (m, 3H), 3.14-3.01 (m, 1H), 2.91-2.82 (m, 1H), 2.79-2.70 (m, 2H), 2.62-2.55 (m, 2H), 2.44-2.30 (m, 2H), 2.27-2.21 (m, 1H), 2.16 (br s, 3H), 2.07-1.89 (m, 1H), 1.49-1.37 (m, 1H) | 661.4 [M + 1]$^+$ |
| 2 | WX002 | $^1$H NMR (400 MHz, CD$_3$OD) δ 8.47 (s, 1H), 7.07-7.38 (m, 6H), 6.82 (d, J = 8.78 Hz, 2H), 4.59 (br s, 1H), 4.47 (d, J = 9.03 Hz, 2H), 4.42 (d, J = 9.54 Hz, 1H), 4.21-4.31 (m, 1H), 3.94-4.07 (m, 2H), 3.35-3.53 (m, 4H), 3.21-3.30 (m, 1H), 2.91-3.09 (m, 3H), 2.62-2.75 (m, 2H), 2.50 (br d, J = 14.31 Hz, 1H), 2.38 (s, 3H), 2.28-2.36 (m, 1H), 2.14 (s, 3H), 1.95-2.04 (m, 1H), 1.64 (q, J = 11.54 Hz, 1H) | 691.1 [M + H]$^+$ |
| 3 | WX003 | $^1$H NMR (400 MHz, CD$_3$OD) δ 8.49 (s, 1 H), 7.30-7.39 (m, 2 H), 7.24 (br d, J = 3.51 Hz, 1 H), 7.17 (dt, J = 9.22, 4.55 Hz, 2 H), 6.99 (d, J = 8.53 Hz, 2 H), 6.77 (d, J = 8.78 Hz, 2 H), 4.54 (d, J = 9.54 Hz, 2 H), 4.39-4.47 (m, 2 H), 4.19-4.28 (m, 3 H), 3.55-3.64 (m, 1 H), 3.51 (t, J = 8.78 Hz, 1 H), 3.35-3.45 (m, 2 H), 3.14-3.24 (m, 1 H), 2.90-3.06 (m, 3 H), 2.58-2.74 (m, 2 H), 2.42-2.53 (m, 1 H), 2.25-2.37 (m, 4 H), 2.15 (s, 3 H), 1.98 (br d, J = 6.78 Hz, 1 H), 1.60 (q, J = 11.54 Hz, 1 H) | 691.1 [M + H]$^+$ |
| 4 | WX004 | $^1$H NMR (400 MHz, CD$_3$OD) δ 8.45 (s, 1 H), 7.09-7.30 (m, 7 H), 6.72-6.87 (m, 2 H), 4.50 (d, J = 9.79 Hz, 1 H), 4.34-4.44 (m, 1 H), 4.26 (br dd, J = 11.04, 2.51 Hz, 1 H), 4.11 (d, J = 9.54 Hz, 1 H), 3.98-4.06 (m, 2 H), 3.33-3.50 (m, 4 H), 2.91-3.11 (m, 3 H), 2.62-2.79 (m, 2 H), 2.52 (br d, J = 13.30 Hz, 1 H), 2.25-2.43 (m, 4 H), 2.10-2.17 (m, 3 H), 1.92-2.05 (m, 1 H), 1.67 (q, J = 11.63 Hz, 1 H), 1.09 (dd, J = 6.78, 2.76 Hz, 1 H) | 691.1 [M + H]$^+$ |
| 5 | WX005 | $^1$H NMR (400 MHz, CD$_3$OD) δ 7.10-7.33 (m, 9 H), 6.82 (d, J = 8.53 Hz, 2 H), 4.63 (br s, 1 H), 4.37-4.47 (m, 2 H), 4.24 (br d, J = 10.79 Hz, 1 H), 4.16 (d, J = 9.29 Hz, 1 H), 3.93 (s, 2 H), 3.36-3.52 (m, 4 H), 3.12-3.22 (m, 1 H), 2.93-3.09 (m, 3 H), 2.61-2.71 (m, 2H), 2.49 (br d, J = 12.05 Hz, 1 H), 2.29-2.41 (m, 1 H), 2.16 (s, 3 H), 1.93-2.04 (m, 1 H), 1.61 (q, J = 11.71 Hz, 1 H) | 643.1 [M + H]$^+$ |
| 6 | WX006 | $^1$H NMR (400 MHz, CD$_3$OD) δ 7.33 (t, J = 8.03 Hz, 1H), 7.18-7.24 (m, 1H), 7.06-7.18 (m, 4H), 6.92 (t, J = 10.04 Hz, 1H), 6.83 (d, J = 8.53 Hz, 2H), 4.46-4.53 (m, 1H), 4.41 (d, J = 9.54 Hz, 1H), 4.30 (d, J = 9.54 Hz, 1H), 4.18-4.24 (m, 1H), 3.93 (s, 2H), 3.45-3.52 (m, 2H), 3.34-3.42 (m, 3H), 2.97-3.05 (m, 2H), 2.89-2.97 (m, 2H), 2.57-2.66 (m, 2H), 2.39-2.47 (m, 1H), 2.28-2.38 (m, 1H), 2.14 (s, 3H), 1.93-2.01 (m, 1H), 1.45-1.56 (m, 1H) | 679.4 [M + H]$^+$ |
| 7 | WX007 | $^1$H NMR (400 MHz, CD$_3$OD) δ 7.23 (br d, J = 8.88 Hz, 2H), 7.07-7.19 (m, 4H), 6.72-6.85 (m, 3H), 4.57-4.67 (m, 2H), 4.29-4.40 (m, 2H), 4.22 (br d, J = 13.26 Hz, 1H), 3.88 (s, 2H), 3.82 (s, 3H), 3.51-3.57 (m, 1H), 3.44-3.50 (m, 1H), 3.35-3.42 (m, 2H), 2.88-3.07 (m, 4H), 2.57-2.68 (m, 2H), 2.44 (br d, J = 12.88 Hz, 1H), 2.33 (br dd, J = 13.20, 6.57 Hz, 1H), 1.91-2.03 (m, 1H), 2.13 (s, 3H), 1.52 (q, J = 11.76 Hz, 1H) | 691.2 [M + H]$^+$ |
| 8 | WX008 | $^1$H NMR (400 MHz, CD$_3$OD) δ 8.49 (s, 1 H), 7.23-7.26 (m, 2 H), 7.09-7.21 (m, 4 H), 6.87 (d, J = 11.01 Hz, 1 H), 6.79 (d, J = 8.75 Hz, 2 H), 4.37-4.46 (m, 3 H), 4.19-4.28 (m, 1 H), 3.89 (s, 2 H), 3.45-3.54 (m, 2 H), 3.34-3.43 (m, 2 H), 3.10-3.22 (m, 1 H), 2.97-3.05 (m, 2 H), 2.90-2.96 (m, 1 H), 2.59-2.71 (m, 2 H), 2.43-2.50 (m, 1 H), 2.36 (s, 3 H), 2.25-2.35 (m, 1 H), 2.12 (s, 3 H), 1.97 (br dd, J = 9.51, 6.63 Hz, 1 H), 1.59 (q, J = 11.67 Hz, 1 H), 1.29-1.34 (m, 1 H) | 675.3 [M + H]$^+$ |

Experimental Embodiment 1. In Vitro Cell Activity Test

Experimental Steps and Methods

Biological Activity Experiment 1: SGLT1 Glucose Transport Assay

1. Experimental Purpose

To test the effect of compounds on the glucose transport activity of SGLT1 transporters by measuring the amount of [$^{14}$C]-labeled glucose entering highly expressed Human-SGLT1 cells.

2. Experimental Methods 2.1. Cell Preparation

The cells stably expressing Human-SGLT1 used for the experiments were constructed by WuXi AppTec Shanghai. The SGLT1 cells were plated in Cytostar-T (PerkinElmer) 96-well cell culture plates and cultured overnight at 5% $CO_2$, 37° C.

2.2. SGLT1 Glucose Transport Assay

Experimental buffer: 10 mM 4-hydroxyethylpiperazine ethanesulfonic acid (HEPES), 1.2 mM magnesium chloride ($MgCl_2$), 4.7 mM potassium chloride (KCl), 2.2 mM calcium chloride ($CaCl_2$) and 120 mM sodium chloride (NaCl).

The compounds were diluted with 100% dimethyl sulfoxide (DMSO) at a starting concentration of 1 mM, 8 points of 5-fold serial gradient dilution was made.

3 μM [$^{14}$C]-labeled methyl α-D-glucopyranoside (Methyl a-D-glucopyranosid) was prepared with experimental buffer.

Cells were treated with 49 μL of experimental buffer, 1 μL of gradient-diluted compound and 50 μL of 3 μM [$^{14}$C]-isotope-labeled glucose solution at 37° C. for 2 hours.

Readings were taken with an isotope detector (Micro beta Reader).

The data were calculated by GraphPad Prism 5.0 software using the formula: log(inhibitor) vs. response—Variable slope to obtain the $IC_{50}$ values of the tested compounds, and the experimental results are shown in Table 5.

Biological Activity Experiment 2: SGLT2 Glucose Transport Assay

1. Experimental Purpose

To test the effect of compounds on the glucose transport activity of SGLT2 transporters by measuring the amount of [$^{14}$C]-labeled glucose entering highly expressed Human-SGLT2 cells.

2. Experimental Methods 2.1. Cell Preparation

The cells stably expressing Human-SGLT2 used for the experiments were constructed by WuXi AppTec Shanghai. SGLT2 cells were plated in 96-well cell culture plates (Greiner) and cultured overnight at 5% $CO_2$, 37° C.

2.2. SGLT2 Glucose Transport Assay

Experimental buffer: 10 mM 4-hydroxyethylpiperazine ethanesulfonic acid (HEPES), 1.2 mM magnesium chloride ($MgCl_2$), 4.7 mM potassium chloride (KCl), 2.2 mM calcium chloride ($CaCl_2$) and 120 mM sodium chloride (NaCl).

Termination buffer: 10 mM 4-hydroxyethylpiperazine ethanesulfonic acid (HEPES), 1.2 mM magnesium chloride ($MgCl_2$), 4.7 mM potassium chloride (KCl), 2.2 mM calcium chloride ($CaCl_2$), 120 mM sodium chloride (NaCl) and 1 μM LX4211.

The compounds were diluted with 100% dimethyl sulfoxide (DMSO) at a starting concentration of 10 μM, 8 points of 5-fold serial gradient dilution was made.

6 μM [$^{14}$C]-labeled methyl α-D-glucopyranoside was prepared with experimental buffer.

Cells were treated with 49 μL of experimental buffer, 1 μL of gradient-diluted compound, and 50 μL of 6 μM [$^{14}$C]-isotope-labeled glucose solution at 37° C. for 2 hours.

The liquid in the wells was aspirated and the cells were washed 3 times with termination buffer.

The cells were lysed with 50 μL of 10% sodium hydroxide solution, and the cell lysate was aspirated into a scintillation tube, and 2 mL of scintillation solution was added.

Readings were taken with an isotope detector (Tricarb).

The data were calculated by GraphPad Prism 5.0 software using the formula: log (inhibitor) vs. response—Variable slope to obtain the $IC_{50}$ values of the tested compounds, and the experimental results are shown in Table 5.

Biological Activity Experiment 3: rhDPP4 Inhibitor Screening Experiment

1. Experimental Purpose

To evaluate the inhibitory activity of compounds against recombinant human dipeptidyl peptidase 4 (rhDPP4) by measuring the half-inhibitory concentration ($IC_{50}$) values of the compounds. In the experiment, rhDPP4 was used to catalyze the generation of fluorescein from substrate, the substrate was a luminescent precursor Gly-Pro-aminofluorescein, and the substrate and luciferase were reacted to generate a light signal, the intensity of the light signal was proportional to the enzyme activity.

2. Experimental Methods

1) The gradient diluted compounds (4-fold fold-dilution, 10 assay concentrations) were transferred 250 nL into a 384-well plate (PerkingElmer-6007299) using a non-contact nano-acoustic pipetting system (ECHO), and dimethyl sulfoxide (DMSO) concentration was 0.5% in the final reaction system. Blank control wells (containing DMSO, substrate and 10 mM Tris-HCl) and positive control wells (containing DMSO, substrate and rhDPP4) were set up.
2) The pre-dispensed frozen buffer containing luciferase was removed and restored to room temperature, and then the substrate was added to configure a working solution with a substrate concentration of 20 μM. RhDPP4 was prepared as a working solution of 0.2 ng/mL using 10 mM Tris-HCl (pH 8.0) aqueous solution.
3) 25 μL of working solution containing 20 μM substrate and 25 μL of working solution containing 0.2 ng/mL rhDPP4 were added to a 384-well plate with the addition of the compound, then the mixture was centrifuged for 30 s at 1000 rpm, the plate was sealed with aluminum foil sealing film and incubated for 1 hour at room temperature.

4) The intensity of the light signal was detected by EnVision, a multifunctional microplate reader. The raw data were used to calculate the inhibition of rhDPP4 activity by the compound.

% of inhibition activity=100−(compound well signal value−blank control well signal value)/(positive control well signal value−blank control well signal value)*100.

The percent of inhibition was imported into GraphPad Prism software for data processing to derive the corresponding dose-effect curves and to derive the $IC_{50}$ values of the tested compounds. The results of the experiments are shown in Table 6.

TABLE 6

Results of in vitro cell activity test

| Compound | Human-SGLT1 $IC_{50}$ (nM) | Human-SGLT2 $IC_{50}$ (nM) | rhDPP4 $IC_{50}$ (nM) |
|---|---|---|---|
| WX001 | 1283 | 21.75 | 31.03 |
| WX002 | 187.5 | 4.84 | 104 |
| WX003 | 980.2 | 332.4 | 111.6 |
| WX004 | 33.34 | 5.96 | 166 |
| WX005 | 28.49 | 5.05 | 115.9 |
| WX006 | 297.80 | 7.02 | 26.9 |
| WX007 | 2070 | 19.73 | 32.54 |
| WX008 | 520.60 | 7.39 | — |

Note:
"—" indicates that no relevant assay is performed.

Conclusion: The Compounds of the Present Disclosure Exhibit High Selectivity Against Human-SGLT2 and Significant Inhibitory Activity Against Human-SGLT2 and rhDPP4 In Vitro Experimental Embodiment 2. In Vivo DMPK Study Experimental purpose: Male C57 mice were used as test animals to determine blood concentrations of compounds and assess pharmacokinetic behavior after a single dose.

Experimental procedure: Six healthy adult male C57 mice were selected, three of them for the intravenous injection group and three of them for the oral group. The compounds to be tested were mixed with an appropriate amount of intravenous injection group solvent (20% polyethylene glycol-400 (PEG400)/10% polyethylene glycol-15 hydroxystearate (solutol)/70% H₂O), the mixture was vortexed and sonicated to obtain 1 mg/mL clarified solution, then the clarified solution was filtered through a microporous membrane and prepared for use; solvent for the oral group was 20% polyethylene glycol-400 (PEG400)/10% polyethylene glycol-15 hydroxystearate (solutol)/70% H₂O, and the compounds to be tested were mixed with the solvent, then the mixture was vortexed and sonicated to obtain 1 mg/mL clarified solution. After 1 mg/kg intravenous administration or 10 mg/kg oral administration in mice, whole blood was collected for a certain period of time, then the plasma was prepared to obtain, and the drug concentration was analyzed by LC-MS/MS method, then the pharmacokinetic parameters were calculated using Phoenix WinNonlin software (Pharsight, USA).

The results of the experiments are shown in Table 7.

TABLE 7

Results of PK tests of compounds

| Compound | $C_{max}$ (nM) | F % | Oral DNAUC (nM · h/mpk) | $Vd_{ss}$ (L/kg) | Cl (mL/min/kg) | $T_{1/2}$ (h) |
|---|---|---|---|---|---|---|
| WX001 | 308 | 21.4 | 194.8 | 12.2 | 31.4 | 7.39 |
| WX006 | 250 | 18.7 | 151.3 | 12.0 | 29.1 | 10.5 |

Note:
$C_{max}$ is the maximum concentration;
F % is the oral bioavailability;
oral unit exposure is Oral DNAUC = $AUC_{PO}$/Dose, $AUC_{PO}$ is the oral exposure, Dose is the drug dose;
$Vd_{ss}$ is the volume of distribution;
Cl is the clearance rate;
$T_{1/2}$ is the half-life.

Conclusion: The Compounds of the Present Disclosure Exhibit to Possess Certain Oral Exposure and Bioavailability for Mice Experimental Embodiment 3. In Vivo Pharmacodynamic Study of Oral Glucose Tolerance (OGTT) in Rats Summary of Experiments 1. Animals

| Animal: | Species: | SD Rat | Sex: | Male |
|---|---|---|---|---|
| | Age/Weight: | About 8 weeks/250 g | Supplier: | Vital River |
| Animal Feed: | General rat/mouse feed | | | |

2. Experimental Grouping

| Group | Compound grouping | Dose | Frequency of administration | Mode of administration | Number of animals per group |
|---|---|---|---|---|---|
| 1 | Vehicle control group | 0 | Single dose | Gavage | 5 |
| 2 | Positive compound (Canagliflozin) | 3 mg/kg | Single dose | Gavage | 5 |
| 3 | Test compound | 10 mg/kg | Single dose | Gavage | 5 |

Experimental Procedure

1. Animal Acclimatization and Preparation

The animals will be acclimatized in the animal room for 1 week after arrival at the facility.

2. Fasting and Drug Administration

The animals are fasted for 16 hours in the metabolic cage and given the drug or solvent (5 mL/kg) according to the table above, followed immediately by 50% glucose solution (2 g/kg, 4 mL/kg).

3. Urinary Glucose and Blood Glucose Test

After 1 hour of glucose administration, the animals resumed feeding, and blood samples were collected at 0 min, 20 min, 40 min, 60 min, 90 min and 120 min for blood glucose measurement; urine at 0 to 24 hours was used for urinary glucose (mg/200 g) and urine volume test, respectively.

4. Data Analysis

All values were expressed as mean values. Statistical analysis was performed using Graphpad Prism 6 single factor analysis of variance Tukey's multiple comparison test. The p-value less than 0.05 was considered statistically significant.

The results of the experiments are shown in Table 8:

TABLE 8

Results of glucose tolerance test in rats

| Compound | Vehicle control group | Positive compound (Canagliflozin) | WX001 |
|---|---|---|---|
| OGTT blood glucose levels $AUC_{0-2hr}$ (mol/L × min) | 1023.9 | 945.2 | 869.0** |
| Urinary glucose level (mg/200 gBW) | 0.6 | 1317**** | 0.7 |
| Urine volume (mL/200 gBW) | 12.5 | 24.4*** | 10.6 |

*refers to p < 0.5,
**refers to p < 0.01,
***refers to p < 0.001,
****refers to p < 0.0001 vs. the vehicle control group.
Note:
200 g BW is 200 g average body weight.

Conclusion: The Compounds of the Present Disclosure Significantly Reduce the Blood Glucose AUC Levels in Animals in 2 Hours Compared to the Vehicle Control Groups; the 24-Hours Urinary Glucose Excretion Levels in Animals are Lower Than Those of the Positive Compound Experimental Embodiment 4. In Vivo Pharmacodynamic Study of Oral Glucose Tolerance (OGTT) in Dbdb Mice

SUMMARY OF EXPERIMENTS

1. Animals

| Animal: | Species: | Dbdb mice | Sex: | Male |
|---|---|---|---|---|
| | Age/Weight: | 11-13 weeks/50 g | Supplier: | Shanghai Model Biology Center |
| Animal Feed: | General rat/mouse feed | | | |

2. Experimental Grouping

| Group | Compound grouping | Dose | Frequency of administration | Mode of administration | Number of animals per group |
|---|---|---|---|---|---|
| 1 | Vehicle control group | 0 | Single dose | Gavage | 5 |
| 2 | Test compound | 50 mg/kg | Single dose | Gavage | 5 |

Experimental Procedure

1. Animal Acclimatization and Preparation

The animals will be acclimatized in the animal room for 1 week after arrival at the facility and grouped according to blood glucose and body weight.

2. Fasting and Drug Administration

The animals are fasted for 6 hours and blood glucose was measured, the drug or solvent were given according to the above table, 50% glucose solution (2 g/kg, 0.4 g/mL) was given after 30 minutes.

3. Test

The bloods at the time points of −30 min, 0 min, 15 min, 30 min, 60 min, 90 min, 120 min of glucose administration were collected and used for blood glucose measurement. At 1 hour of glucose administration, blood was taken to detect insulin secretion, and at 2 hours of glucose administration, animals were euthanized and blood was taken to detect DPP4 activity and active GLP-1.

4. Data Analysis

Statistical analysis was performed using Graphpad Prism 8 unpaired T-test for comparison, and the p-values less than 0.05 were considered statistically significant.

Data are expressed as mean±standard error, n=4-5. Experimental results are shown in FIGS. 1, 2, 3, 4, and 5. In the drawings, *refers to p<0.5, refers to p<0.01, *refers to p<0.001, and ****refers to p<0.0001 vs. the vehicle control group.

Conclusion: The Compounds of the Present Disclosure Compared to the Vehicle Control Significantly Reduce the Blood Glucose AUC Levels in Animals in 2 Hours, Significantly Increase Insulin as Well as Active GLP-1 Levels, and Reduce DPP4 Activity Experimental Embodiment 5. In Vivo Pharmacodynamic Study of Oral Glucose Tolerance in BKS-db Mice on a High-Sugar and High-Fat Diet Summary of Experiments

1. Animals

| Animal: | Species: | BKS-db | Sex: | Male |
|---|---|---|---|---|
| | Age | 7 weeks | Supplier: | Jiangsu Jicui Yaokang Biological Technology Co., Ltd. |
| Animal Feed: | 45% HF + 17% HS (RDI #D12451) | | | |

2. Experimental Grouping

| Group | Compound grouping | Dose | Frequency of administration | Mode of administration | Number of animals per group |
|---|---|---|---|---|---|
| 1 | Normal control group (control) | 0 | QD | Gavage | 3 |
| 2 | Vehicle control group (Vehicle) | 0 | QD | Gavage | 8 |
| 4 | Test compound | 50 mg/kg | QD | Gavage | 8 |

3. Experimental Procedure

After adaptive feeding of 7-week-old BKS and BKS-db mice, and the blood was collected after fasting for 6 hours, then fasting blood glucose and HbA1c were detected. Mice were grouped according to HbA1c of 6 hours fasting (primary reference index), fasting blood glucose and body weight (secondary reference index).

At the 2nd week of administration, fasting blood glucose was detected after fasting for 6 hours, and postprandial blood glucose was detected after 1 hour of resumption of feeding; at the 4th week of administration, fasting blood glucose was detected after fasting for 6 hours, and postprandial blood glucose and HbA1c were detected after 1 hour of resumption of feeding; urine was collected from each group of mice. After animals were euthanized, livers were taken for oil red staining and steatosis scoring.

4. Data Analysis

Statistical analysis was performed using Graphpad Prism 8, One Way ANOVA or unpaired T test for comparison, the p-values less than 0.05 were considered statistically significant.

Figure 6:
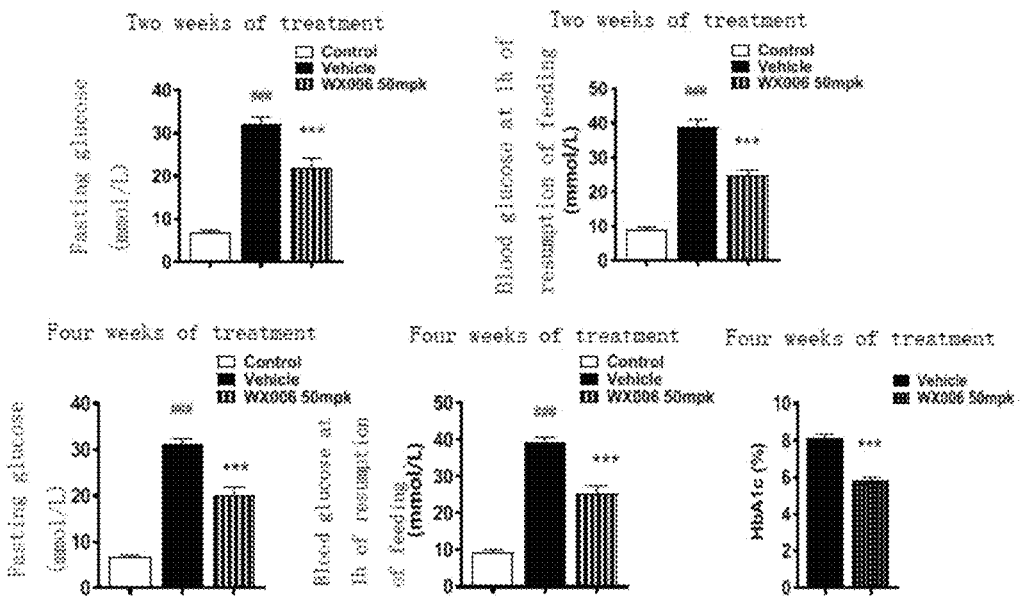
FIG. 6 is the blood glucose control after 2 and 4 weeks of administration.
Figure 7:
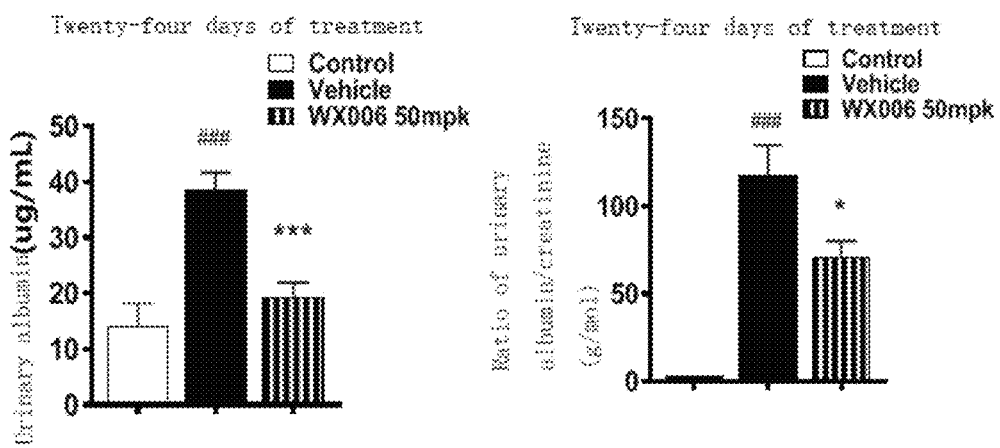
FIG. 7 is the changes of urinary albumin and urinary creatinine after 24 days of administration.
Figure 8:
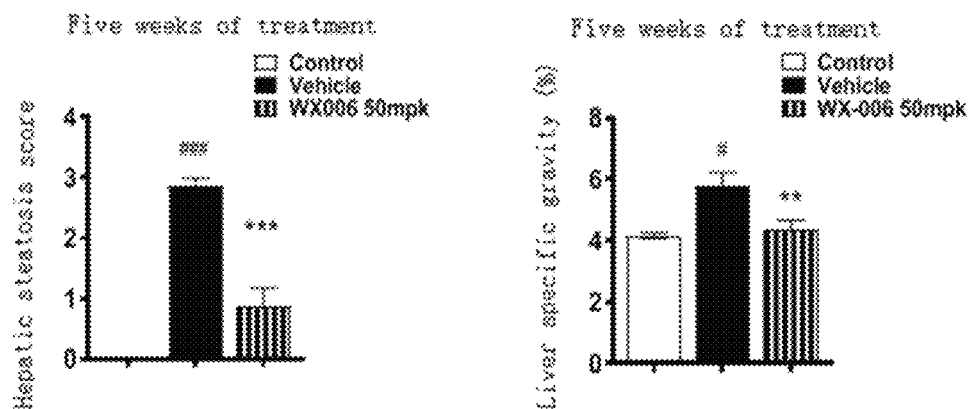
FIG. 8 is the hepatic steatosis and liver specific gravity after 5 weeks of administration.
Figure 8:
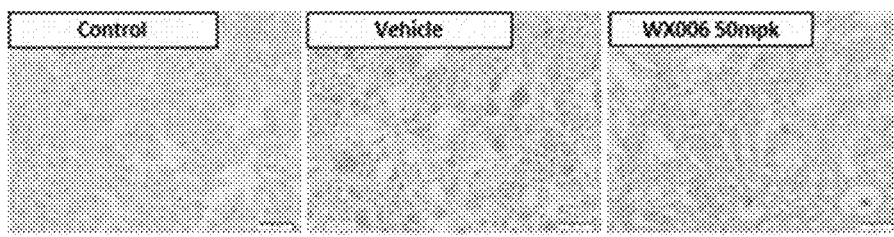

Data are expressed as mean±standard error, n=3-8. Experimental results are shown in FIGS. 6, 7 and 8. In the drawings, "##" refers to p<0.01 "###" refers to p<0.001 vs. the normal control group; "*" refers to p<0.5, "" refers to p<0.01, "*" refers to p<0.001, "****" refers to p<0.0001 vs. the vehicle control group.

Conclusion

FIG. 6 shows that the compounds of the present disclosure have significant hypoglycemic effect; FIGS. 7 and 8 show that the compounds of the present disclosure have nephroprotective effect.

What is claimed is:

1. A compound of formula (I), a stereoisomer thereof, or a pharmaceutically acceptable salt thereof,

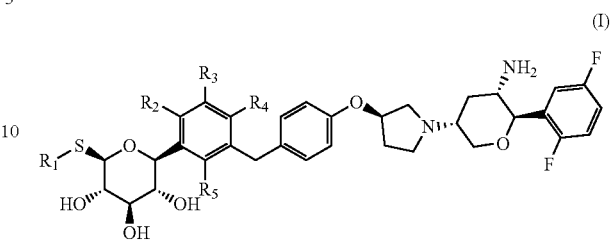

(I)

wherein, $R_1$ is $C_{1-3}$ alkyl, which is optionally substituted by 1, 2, or 3 $R_a$;

$R_2$ and $R_3$ are each independently selected from H, F, Cl, Br, I, OH, $NH_2$, $C_{1-3}$ alkyl, and $C_{1-3}$ alkoxy, wherein the $C_{1-3}$ alkyl and the $C_{1-3}$ alkoxy are optionally substituted by 1, 2, or 3 $R_b$;

$R_5$ is selected from H, F, Cl, Br, I, OH, $NH_2$, and $C_{1-3}$ alkyl, wherein the $C_{1-3}$ alkyl is optionally substituted by 1, 2, or 3 $R_c$;

$R_4$ is H, F, or Cl, and when $R_4$ is Cl, $R_2$, $R_3$, and $R_5$ are not H at the same time;

$R_a$, $R_b$ and $R_c$ are each independently selected from F, Cl, Br, I, OH, and $NH_2$.

2. The compound, the stereoisomer thereof, or the pharmaceutically acceptable salt thereof as defined in claim 1, wherein, $R_1$ is $CH_3$, which is optionally substituted by 1, 2, or 3 $R_a$.

3. The compound, the stereoisomer thereof, or the pharmaceutically acceptable salt thereof as defined in claim 2, wherein, $R_1$ is $CH_3$.

4. The compound, the stereoisomer thereof, or the pharmaceutically acceptable salt thereof as defined in claim 1, wherein, $R_2$ and $R_3$ are each independently selected from H, F, Cl, Br, I, OH, $NH_2$, $CH_3$, Et, and —$OCH_3$, wherein the $CH_3$, Et, and —$OCH_3$ are optionally substituted by 1, 2, or 3 $R_b$.

5. The compound, the stereoisomer thereof, or the pharmaceutically acceptable salt thereof as defined in claim 4, wherein, $R_2$ and $R_3$ are each independently selected from H, F, Cl, Br, I, OH, $NH_2$, $CH_3$, Et, and —$OCH_3$.

6. The compound, the stereoisomer thereof, or the pharmaceutically acceptable salt thereof as defined in claim 1, wherein, $R_5$ is selected from H, F, Cl, Br, I, OH, $NH_2$, $CH_3$, and Et, wherein the $CH_3$ and Et are optionally substituted by 1, 2, or 3 $R_c$.

7. The compound, the stereoisomer thereof, or the pharmaceutically acceptable salt thereof as defined in claim 6, wherein, $R_5$ is selected from H, F, Cl, Br, I, OH, $NH_2$, $CH_3$, and Et.

8. A compound, a stereoisomer thereof, or a pharmaceutically acceptable salt thereof as follows,

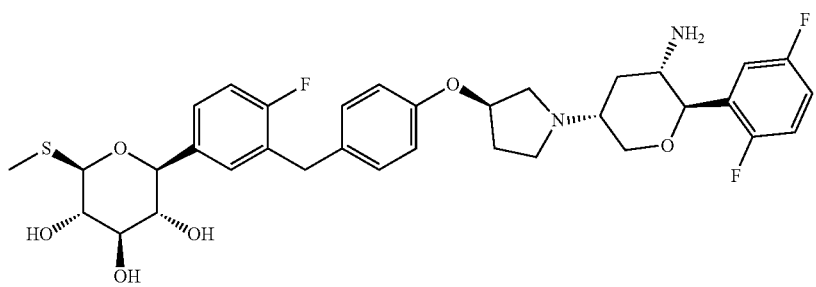

,

-continued
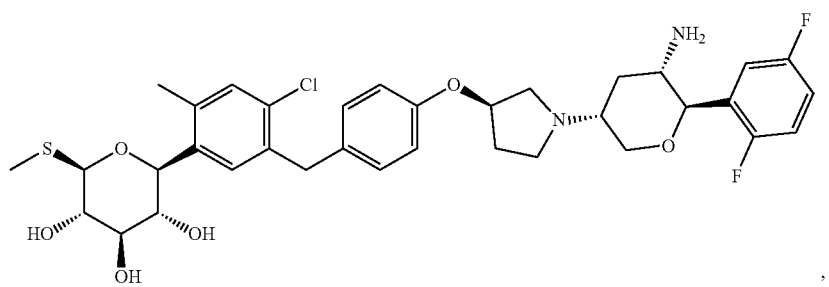
,
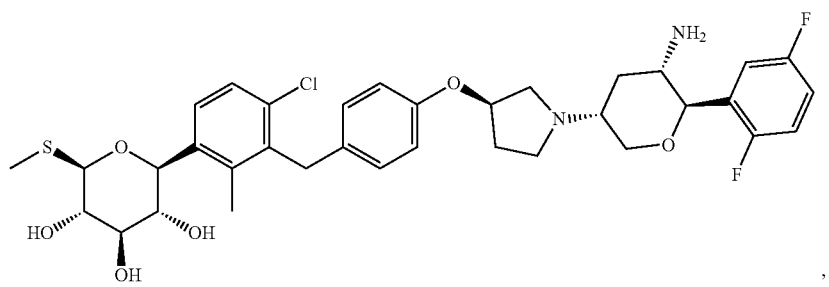
,
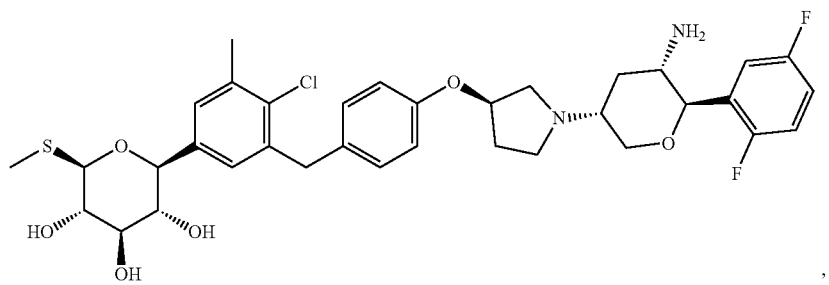
,
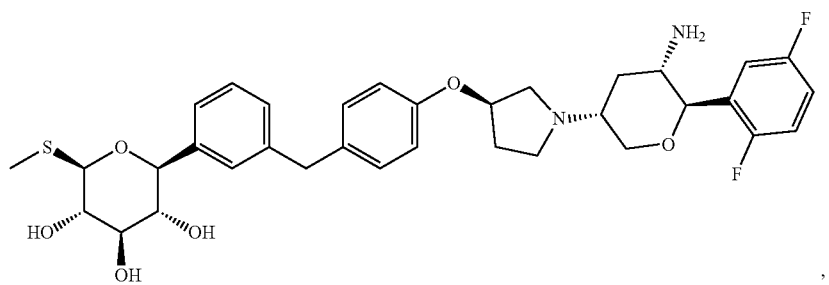
,
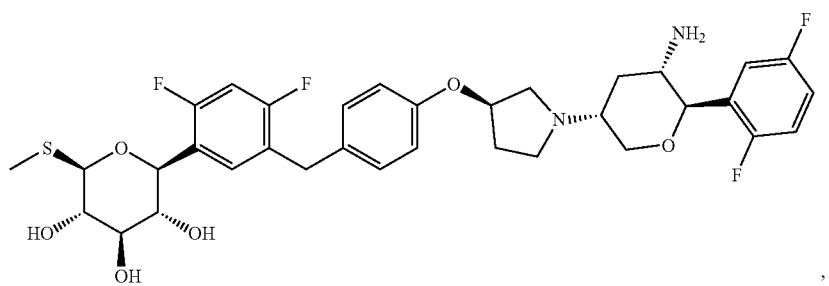
,
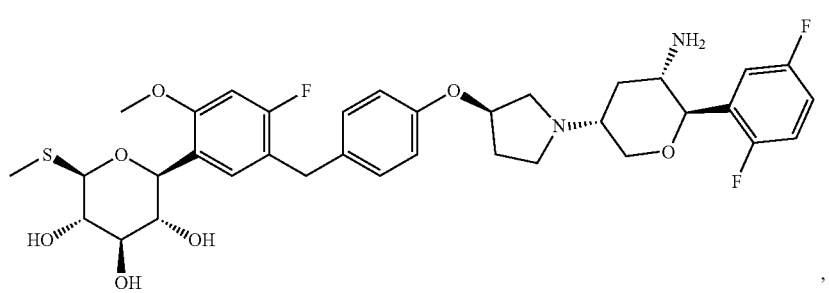
, or -continued
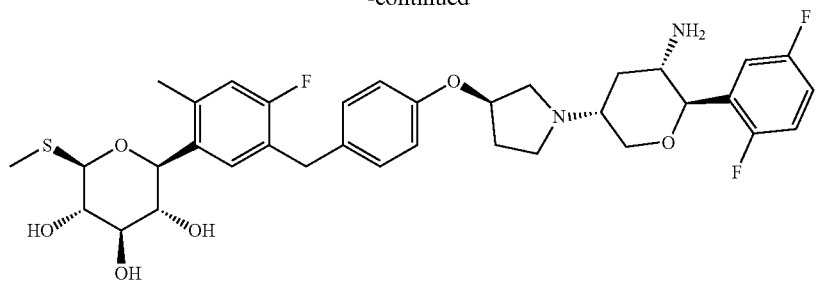
9. A method of inhibiting SGLT2 and DPP4 in a subject in need thereof, comprising administering the compound, the stereoisomer thereof, or the pharmaceutically acceptable salt thereof as defined in claim 1 into the subject.
* * * * *